United States Patent [19]
Wenstrom, Jr.

[11] Patent Number: 5,578,057
[45] Date of Patent: Nov. 26, 1996

[54] ANCHORING DEVICE INSTALLATION TOOL ASSEMBLY AND METHOD

[75] Inventor: Richard F. Wenstrom, Jr., Attleboro, Mass.

[73] Assignee: Mitek Surgical Products, Inc., Westwood, Mass.

[21] Appl. No.: 98,599

[22] Filed: Jul. 28, 1993

[51] Int. Cl.$^6$ .................................................. A61B 17/04
[52] U.S. Cl. ......................... 606/232; 606/104; 606/144; 606/139
[58] Field of Search .................................. 606/232, 143, 606/144, 148, 139, 213, 72, 74, 104, 146

[56] References Cited

U.S. PATENT DOCUMENTS

| | | | |
|---|---|---|---|
| 3,361,382 | 1/1968 | Converse | 606/148 |
| 4,968,315 | 11/1990 | Gatturna | 606/139 |
| 5,002,550 | 3/1991 | Li | 606/139 |
| 5,021,059 | 6/1991 | Kensey et al. | 606/232 |
| 5,100,417 | 3/1992 | Cerier et al. | 606/232 |
| 5,217,486 | 6/1993 | Rice et al. | 606/232 |
| 5,222,974 | 6/1993 | Kensey et al. | 606/213 |
| 5,224,946 | 7/1993 | Hayhurst et al. | 606/232 |

*Primary Examiner*—Gary Jackson
*Attorney, Agent, or Firm*—Pandiscio & Pandiscio

[57] ABSTRACT

An installation tool for deploying an anchoring device in a preformed hole in a workpiece is provided. The anchoring device is attached to a portion of a length of cord-like material carrying a needle-like member about at least one of its free ends. A retention device defining a continuous groove around an axle; a retention groove defined by circumferentially spaced arcuate projections from at least one of its end surfaces; and a notch forming a pathway connecting the continuous groove with the retention groove also is provided. The needle-like member and the free end of the cord-like material are releasably located in the retention groove, the cord-like material is passed through the notch, and the cord-like material extending from the fastening device is wrapped around the axle. The retention device is also releasably attachable to the handle of the installation tool. In use, the free end(s) of the cord-like material and the needle-like member(s) are held by the retention device mounted on the handle of the installation tool during the insertion of the anchoring device. Thereafter, the retention device may be detached from the handle, and kept in the vicinity of the hole until the free end(s) of the cord-like material and the needle-like member(s) are required for use in attaching an object to the workpiece. In the preferred embodiments, the fastening device is a suture anchor, the workpiece is bone, the cord-like material is suture, and the needle-like members are curved surgical needles.

16 Claims, 17 Drawing Sheets

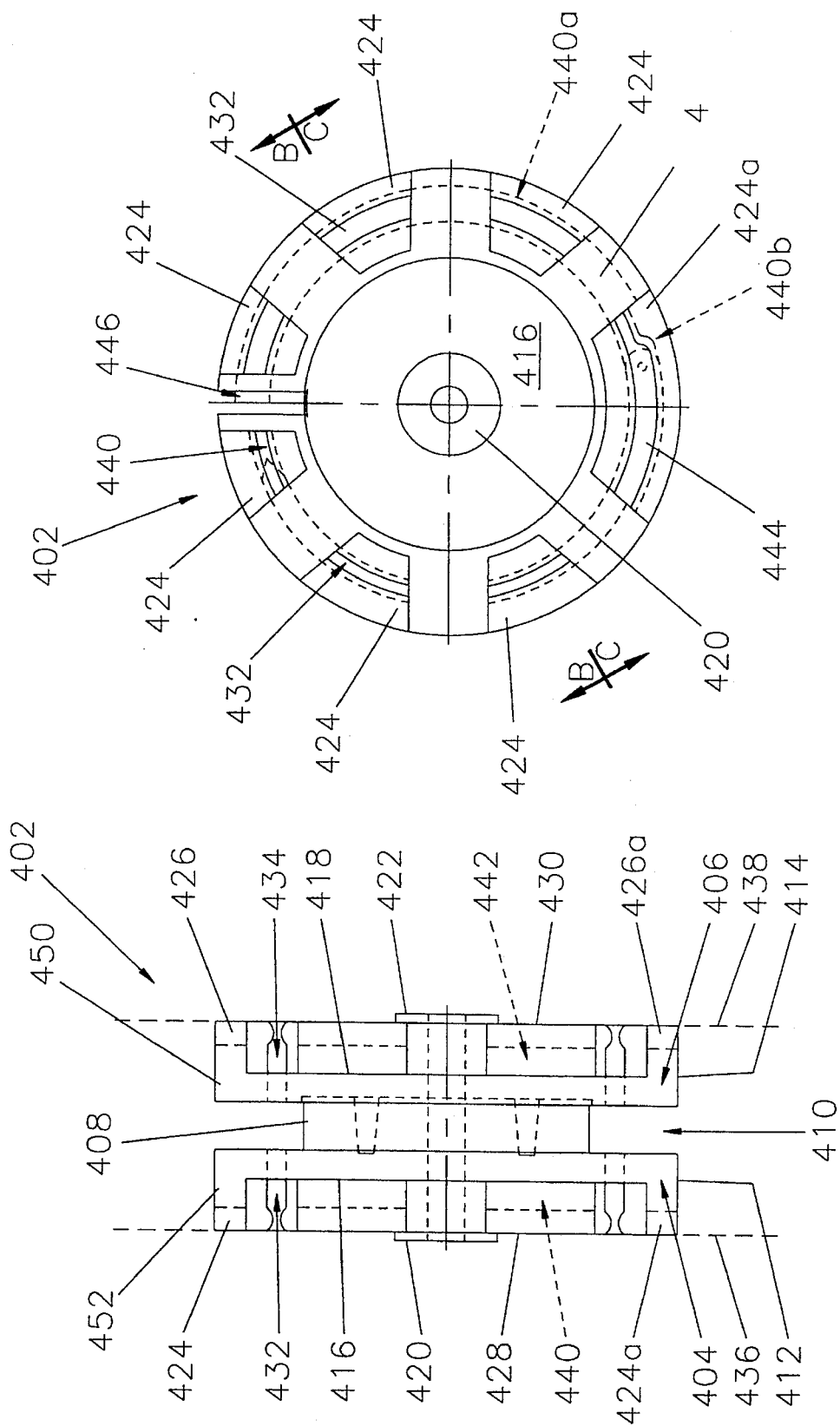

ANCHORING DEVICE INSTALLATION TOOL ASSEMBLY AND METHOD

FIELD OF THE INVENTION

This invention generally relates to installation tools for deploying anchoring devices within preformed holes in workpieces. More particularly, the invention relates to installation tools of the type including retention means for holding free ends of lengths of cord-like material extending from the anchoring device, and such needle-like elements as may be attached thereto. Still more particularly, the invention relates to suture anchor installation tools.

SUMMARY OF THE PRIOR ART

In U.S. Pat. No. 4,898,156, issued on Feb. 6, 1990 to Gatturna et al.; U.S. Pat. No. 4,899,743, issued on Feb. 13, 1990 to Nicholson et al.; U.S. Pat. No. 4,946,468, issued on Aug. 7, 1990 to Li; U.S. Pat. No. 4,968,315, issued on Nov. 6, 1990 to Gatturna; U.S. Pat. No. 5,002,550, issued on Mar. 26, 1991 to Li; U.S. Pat. No. 5,046,513, issued on Sep. 10, 1991 to Gatturna et al.; U.S. patent application Ser. No. 07/902,513, filed Jun. 22, 1992 by Li (a continuation of U.S. patent application Ser. No. 07/766,025, filed Sep. 26, 1991); and U.S. patent application Ser. No. 07/837,061, filed Feb. 18, 1992 by Rice et al., there are disclosed a variety of anchors for positioning one end (or an intermediate portion) of a length of suture within a preformed hole in bone. The foregoing patents and patent applications also disclose several installation tools for deploying the respective suture anchors disclosed therein. Further, some of these tools include a handle adapted to hold portions of free suture ends extending from the anchor and such needles as may be attached to those free ends. Complete details of the construction and operation of these anchors and installation tools are provided in the above-identified patents and patent applications, the disclosures of which are incorporated herein by reference. The above-identified patents and patent applications are all owned by Mitek Surgical Products, Inc., of Norwood, Mass., the assignee of this application.

Still other suture anchors and suture anchor installation tools are described and illustrated in U.S. Pat. No. 4,632,100 issued on Dec. 30, 1986 to Somers et al.; U.S. Pat. No. 4,738,255 issued on Apr. 19, 1988 to Goble et al.; and U.S. Pat. No. 4,741,330 issued on May 3, 1988 to Hayhurst. The disclosures of these patents also are incorporated herein by reference.

The primary purpose of all of the foregoing devices is to provide attachment means for positioning, and substantially fixedly attaching, a portion of a length of suture to a piece of bone. The use of "traditional" attachment means—such as nails, screws and staples—for this purpose are not totally satisfactory for various reasons. In particular, "traditional" attachment means often penetrate through, and undesirably damage, the object during the attachment procedure. Further, such "traditional" attachment means do not reliably assure that an initially secure attachment will not loosen or fail when subjected to normal stresses during the healing process. In view of these and other problems, anchors designed for substantially permanently locating a portion of at least one length of suture within a preformed hole in bone have been widely adopted.

The development of such suture anchors has included the design of associated installation tools for deploying the anchors. Such tools invariably include components sized for entry into the bone hole. This allows the anchor to be carried (or driven) to a desired anchoring location within the bone hole. Further, many such tools are designed to engage an anchor in a manner which allows it to be conveniently conveyed to the hole in the bone.

The popularity of suture anchors has resulted in a growing desire to deploy smaller and smaller suture anchors in smaller and smaller bones. In response to these desires, suture anchors and their associated installation tools have evolved over time.

The design of early suture anchor installation tools contemplated that the portion of the tool which engaged the anchor for transport to the bone hole would also carry the anchor to its desired anchoring location in the bone hole. As anchor-receiving holes have become smaller, however, the design and manufacture of such tools has become more and more difficult. Accordingly, in a more recent version of such tools, which is disclosed in the aforementioned U.S. patent application Ser. No. 07/837,061, a tubular element is provided to engage and convey the anchor to the hole formed in the bone. Typically, the distal end of this tubular element has a transverse cross-section too large to permit it to enter the bone hole. Therefore, other associated elements (i.e., plungers) are provided to drive the anchor away from the tubular element and into its desired final location in the target hole.

Surgical procedures utilizing the foregoing types of installation tool, however, still are impaired by the free ends of suture (with or without needles attached thereto) extending from the anchor. This is because once the anchor has been deployed, the free suture ends extend from the anchor into areas immediately adjacent to the operative field. Such free suture ends may easily become tangled. Further, any needle(s) attached to these free ends may inadvertently injure surgical personnel. Still further, the needle(s) are not always maintained in locations which are conveniently and readily available to the surgeon.

In response to the latter problems, handles have been designed for suture anchor installation tools which releasably hold both the free suture ends extending from the anchor, and such needles as may be attached thereto. Tools including such handles, however, are relatively expensive and difficult to assemble. In particular, the loading of free suture ends and such needles as may be attached thereto into such handles must be carefully done. This is because the free suture ends must be easily pulled from the handle without tangling, binding or jamming once the anchor has been "set" in the bone hole. As a practical matter, therefore, currently available installation tools with suture and needle holding handles are manufactured in a preloaded condition and as "throw away" devices. This effectively increases the cost of surgical procedures using such tools in comparison to cases in which reusable tools can be used.

Further, presently available suture anchor installation tools including suture/needle holding handles are comparatively large. Accordingly, while the handles are needed to hold the needles in a readily available position for use by the surgeon with a minimum danger of injury to surgical personnel, they also tend to impede access to the operative field. One result of this is that such installation tools are subject to being inadvertently pushed about or dropped. Such accidents can be disruptive of the surgical procedure. They also may seriously damage the tool and/or prematurely dislodge the suture and needles from the handle.

OBJECTS OF THE INVENTION

In view of the foregoing problems, the primary object of the present invention is to provide an installation tool which improves upon the constructions shown in U.S. Pat. Nos. 4,946,468 and 5,002,550.

It also is an object of the present invention to provide a suture anchor installation tool including suture/needle retention means which is releasably attachable to the tool.

Another object of the present invention is to provide a suture anchor installation tool wherein (a) an anchor is engaged for transport to a hole in a bone by a first element; (b) the anchor is inserted into the bone hole by a second element, the second element operating in association with the first element and the outer surface of the bone; and (c) the free suture and any object or objects attached thereto (e.g. a needle or needles) is (are) held by a third element.

Yet another object of the present invention is to provide a new and improved anchoring system for attaching objects to a bone.

Still another object of the present invention is to provide a new and improved method for attaching an object to bone with an anchor.

SUMMARY OF THE INVENTION

These and other objects of the invention are achieved by the provision and use of a novel anchor installation tool. In the preferred embodiment, the tool is adapted to deploy a suture anchor in a preformed hole in a piece of bone (hereinafter sometimes referred to as a "bone hole").

Also in the preferred embodiments, it is contemplated that the anchor will be of the type including (a) a body, (b) at least one barb and (c) attachment means for connecting a portion of a length of cord-like material (suture) to the body. In such devices, the barbs may be attached to the body in spaced, circumferential relation one to the other. Further, the barbs extend rearwardly and outwardly from the body to respective outer ends. These outer ends are normally located outwardly of an axial projection of the maximum geometric cross-section of the body, taken perpendicular to its longitudinal axis. This assures that each barb will engage the side wall of the target hole within which the anchor is to be set. Specifically, each of the barbs is elastically deformable. Accordingly, each barb may be deflected from its normal, unstressed configuration (just described) toward a deformed, stressed configuration as it is located in the bone hole. In the latter configuration, the barb may be located substantially within an axial projection of the maximum cross-section of the body referred to above. Thereafter, once the body is located at the desired position in the bone hole, the barbs are allowed to spring back toward their unstressed configuration so as to bind the body to the side walls of the bone hole. In the preferred embodiment of the invention, the anchoring device is a suture anchor.

The novel installation tool of the invention includes (1) positioning means for engaging an anchor and locating the anchor at a desired position within a hole in a workpiece, and (2) retention means releasably associated with the positioning means. The retention means is adapted to releasably hold free ends of a cord-like material extending from the anchor. The retention means is also adapted to hold such needle-like members as may be attached to the free ends of the cord-like material. Further, it is contemplated that this retention may be maintained both during the insertion of the anchor and thereafter. Still further, the invention contemplates that after the anchor is inserted into the bone hole, the retention means may be utilized either alone, or in association with the remainder of the tool.

In the preferred embodiment of the invention, the installation tool is designed to insert a suture anchor into a preformed bone hole. More particularly, the preferred embodiment includes (1) means for engaging a suture anchor in a manner which allows it to be conveniently conveyed to the opening of a hole in the surface of a bone; (2) means for locating the anchor at a desired position within the bone hole; and (3) means for retaining at least one length of suture extending from the anchor, and for retaining any needle(s) attached thereto, both during the anchor insertion operation, and thereafter.

Specifically, the preferred embodiment of the invention, contemplates that the anchor engagement means comprises a tubular element, the locating means comprises a shaft having a handle attached to its proximal end, and the retention means comprises a bobbin-like member. The tubular element is adapted to receive and hold a co-axially oriented portion of a suture anchor in its distal end. The shaft is located in the lumen of the tubular element and is movable between a first, retracted position and a second, extended position.

In the first, retracted position, the distal end of the shaft resides in proximally spaced relation to the distal end of the tubular element within the lumen. In the second, extended position, the distal portion of the shaft extends distally of the distal end of the tubular element. The transverse cross-section of the distal portion of the shaft is selected to be smaller than the transverse cross-section of the bone hole. The transverse cross-section of the distal end of the tubular element, on the other hand, is selected to be larger than the transverse cross-section of the bone hole.

Accordingly, when the tool is in its first, retracted position, the distal portion of an anchor located and held in the distal end of the tubular element may be conveyed to, and located in, the bone hole. Then, while holding the distal end of the tubular element in contact with the surface of the bone, the shaft may be moved to its second, extended position relative to the tubular element. This movement of the shaft ejects the anchor from the tool, and forces the anchor to a desired position within the bone hole.

The handle has a distal end, a distal portion adjacent the distal end, a pair of opposing, substantially identical arms extending proximally from the distal portion, and a wall portion. Each arm defines a substantially planar, inwardly facing surface and a substantially cylindrical bore. The planar surfaces are oriented substantially parallel to one another. The wall portion is oriented in a plane perpendicular to the longitudinal axis of the tool, and transversely connects the arms substantially midway along their axial lengths. The bores are centered on a common axis perpendicular to the longitudinal axis of the tool, and are spaced rearwardly of the connecting wall. Further, suture guiding notches are provided along the sides of the tool between the arms in order to maintain the orientation of the portion(s) of the suture which extend(s) between the anchor and the retention means during the anchor installation procedure.

The bobbin-like member includes a pair of opposing, generally cylindrical, side portions connected in parallel, spaced relation to each other by an axle portion. The bobbin-like member, therefore, defines a centered, continuous groove between the opposing side portions.

Each of the side portions defines a peripheral edge and an outwardly facing, circular end surface. An axially oriented, substantially cylindrical projection extends outwardly from each of the end surfaces. In addition, a plurality of arcuate projections extend outwardly from each of the end surfaces parallel to, but a distance shorter than, the axial projections therefrom. The arcuate projections are located adjacent to the peripheral edge of their associated side portion. They are also spaced from the axial projection of their associated side portion, and circumferentially spaced one from the other.

Each of the arcuate projections defines an outer surface and an arc-shaped slot. The outer surfaces of the arcuate projections are located in common planes which are spaced outwardly from, and parallel to, the end surface of the respective side portions. The slots each extend through their associated arcuate projection in concentric spaced relation to the peripheral edge of their associated side portion, and inwardly from the outer surface of the projection through the associated side portion to the continuous groove. Together, these arc-shaped slots define broken, circular grooves which are spaced radially inwardly of the peripheral edges of their respective associated side portions.

Each of the broken grooves is adapted to releasably receive and hold a curved surgical needle and/or a free end of suture. Still further, at least one of the side portions defines a notch extending into its peripheral edge between a selected pair of the arcuate projections. This notch opens into both the continuous groove and the end surface of its associated side portion.

The bobbin-like member, therefore, is adapted to hold a portion of a length of suture wrapped around the axle in the continuous groove. Another portion of that length of suture extends from the continuous groove to the attachment means of the anchor. Still another portion of that length of suture extends from the continuous groove through the notch to a surgical needle which is releasably located in the broken groove defined by the arcuate projections. The needle is removable from the groove by inserting a needle grasping device into one of the spaces between the arcuate projections. Such a grasping device may engage the portion of a needle extending through that space. Thereafter, the exertion of an outwardly directed axial force on the grasping means will withdraw the needle from the broken groove defined by the arcuate projections. If desired, a curved surgical needle and/or a free end of suture may be positioned in each of the broken grooves defined by the arcuate projections.

The bobbin-like member is also releasably and rotatably maintained between the planar surfaces of the arms of the handle. This is accomplished by a snap-fit engagement of the outwardmost portions of the axial projections of the bobbin-like member with the bores in the respective arms of the handle. The bobbin-like member may be disengaged from the handle by applying inwardly directed pressure to the portions of the arms located between the distal portion of the handle and the connecting wall. This pressure (i) bends the portions of the arms located between the distal portion of the handle and the connecting wall inwardly; (ii) pivots the portions of the arms located proximally of the connecting wall about the edges of the wall attached to the arms, and (iii) moves the bores away from each other. This frees the axial projections from the bores, and allows the bobbin-like member to be slid along the planar surfaces until it is disengaged from the tool. The bobbin-like member can be rotatably mounted between the arms of the handle by reversing the procedure just described.

The method of attaching an object to a bone utilizing the device of the present invention includes the steps of:

(a) providing an assembly comprising:
(i) an anchoring device adapted for fixed location within a preformed hole in the bone;
(ii) a length of cord-like material, the length of cord-like material having at least one free end and a portion attached to the anchoring device;
(iii) at least one needle-like member attached to the at least one free end of the length of cord-like material; and
(iv) an installation tool for deploying the anchoring device within the preformed hole in the bone, the installation tool comprising positioning means and retention means wherein:
the positioning means includes a handle, releasably engages the anchoring device and is adapted for locating the anchoring device at a predetermined depth within the preformed hole in the bone; and
the retention means is releasably attached to the handle of the positioning means and releasably holds the at least one needle-like member and at least the portion of the length of cord-like material adjacent to its at least one free end;

(b) manipulating the installation tool so as to locate the anchoring device at a preselected depth within the preformed hole in the bone with the positioning means;

(c) manipulating the installation tool so as to disassociate the positioning means from the bone and to disengage the portion of the length of cord-like material adjacent to its at least one free end from the retention means;

(d) detaching the retention means from the handle of the positioning means;

(e) disengaging the at least one free end of the length of cord-like material and the at least one needle-like member from the retention means; and (f) manipulating the at least one free end of the length of cord-like material and the at least one needle-like member so as to attach the object to the bone.

BRIEF DESCRIPTION OF THE DRAWINGS

These and other features, objects and advantages of the present invention will become clear to those skilled in the art in view of the following detailed description of a preferred embodiment of the invention. This detailed description is to be read in conjunction with the appended drawings, wherein like numbers are used to designate like elements throughout, and wherein:

FIG. 10 is a side view of the bobbin-like element of the installation tool generally shown in FIG. 1;

FIG. 11 is an end view of the bobbin-like member shown in FIG. 10;

DETAILED DESCRIPTION OF THE PREFERRED EMBODIMENT

Figure 1:
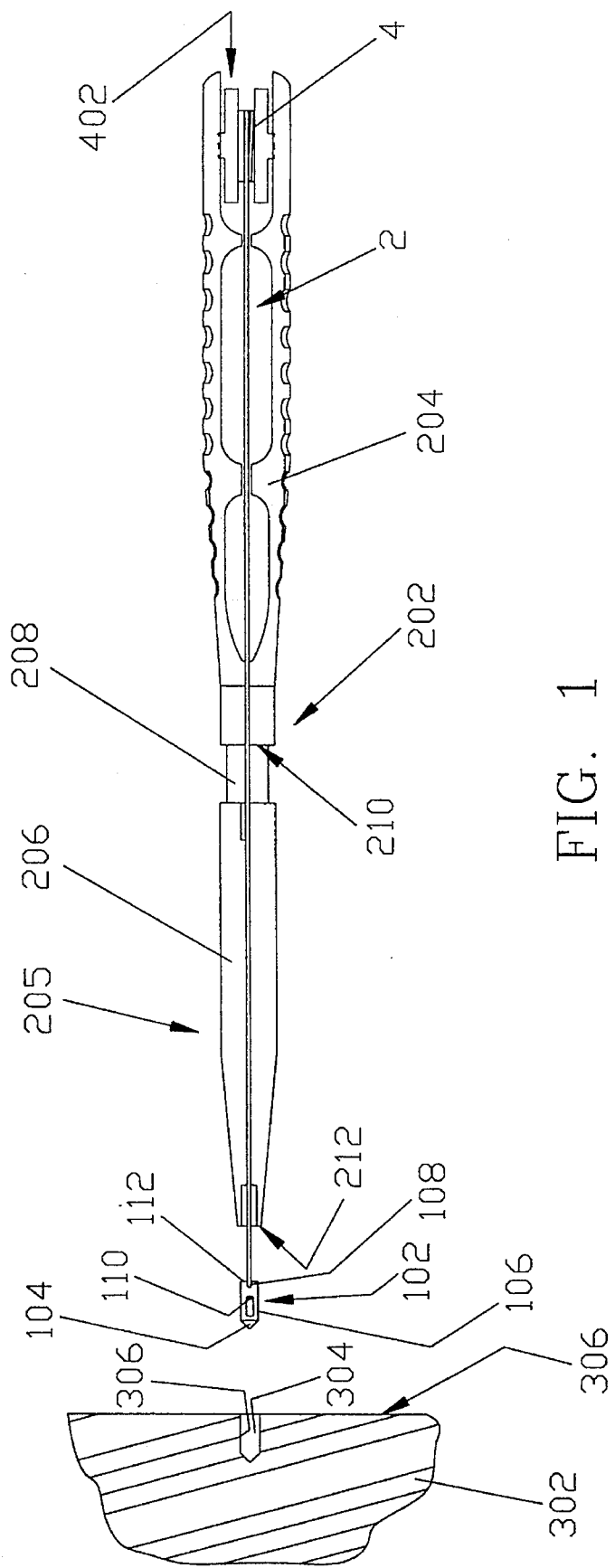
FIG. 1 is an illustrative, exploded side view of an installation tool formed in accordance with the invention, a representative suture anchor connected to a bobbin-like member at the proximal end of the tool by a length of suture, and a piece of bone.

Referring now to the drawings, and particularly to FIG. 1, there are shown in exploded, illustrative relation to one another, a suture 2, a suture anchor 102, a suture anchor installation tool 202 and a target bone 302 having a hole 304 formed therein. Suture 2 is attached to suture anchor 102. Installation tool 202 is adapted to position anchor 102 in hole 304 formed in target bone 302. Installation tool 202 also includes a handle 204 adapted to releasably hold a bobbin-like element 402. Bobbin-like element 402 is adapted to releasably hold the free end(s) 4 of suture 2 and any curved surgical needles which may be attached thereto, as will hereinafter be described in detail.

It is to be noted at the outset that anchor 102 and anchor positioning portion 205 of installation tool 202 may take any one of several forms well known in the art without departure from the present invention. Accordingly, it will be understood that the specific anchor 102 and anchor positioning portion 205 of installation tool 202 described in detail below are presented as being illustrative only, and not as limiting of the invention in its broadest aspects. These features of the preferred embodiment will be described first in order to establish a working context for the detailed description of the novel features of the invention.

Anchor 102 is representative of the preferred type of anchoring devices which are to be installed by installation tool 202. Such anchors typically include (a) a body 104, (b) at least one barb 106, and (c) attachment means 108 for connecting a portion of a length of cord-like material (i.e., suture 2) to body 104. In the drawing, connection means 108 is shown as a bore extending through the proximal portion of body 104 (see, for example, U.S. Pat. No. 4,898,156 and U.S. patent application Ser. No. 07/902,513).

In such anchoring devices, barbs 106 are attached to body 104 in spaced, circumferential relation one to the other. Further, barbs 106 each extend rearwardly and outwardly from body 104 to respective outer ends 110. Outer ends 110 are normally located outwardly of an axial projection of the maximum, geometric, transverse cross-section of body 104. This assures that each barb 106 engages side wall 306 of target hole 304. Each of the barbs 106 is elastically deformable. Accordingly, each barb 106 may be deflected from its normal, unstressed configuration (just described) toward a deformed, stressed configuration. In the latter configuration, each barb is located substantially within the axial projection of the maximum transverse cross-section of body 104. As noted above, in the preferred embodiment of the invention, the fastening device is a suture anchor, and the workpiece is a piece of bone.

Figure 7:
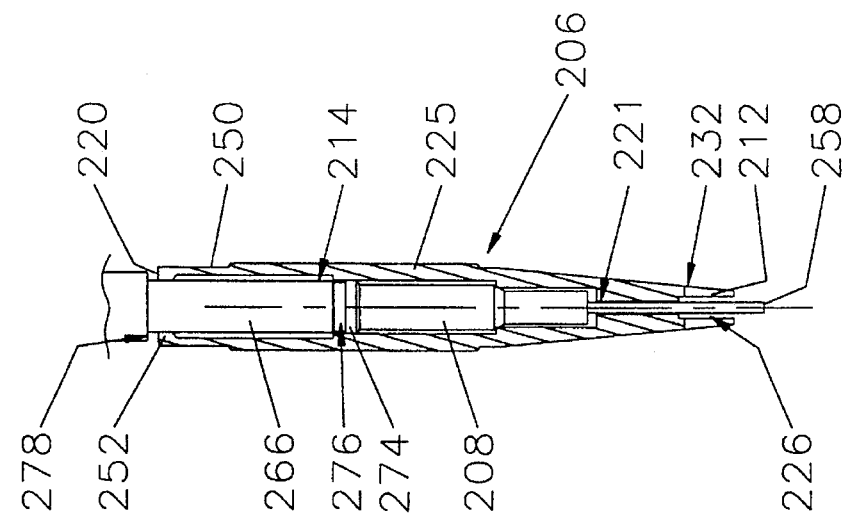
FIG. 7 is a side view, in partial section and partially cut away, showing the tubular element of FIG. 2 and the shaft of FIG. 5 in a second, extended position relative to one another.
Figure 8:
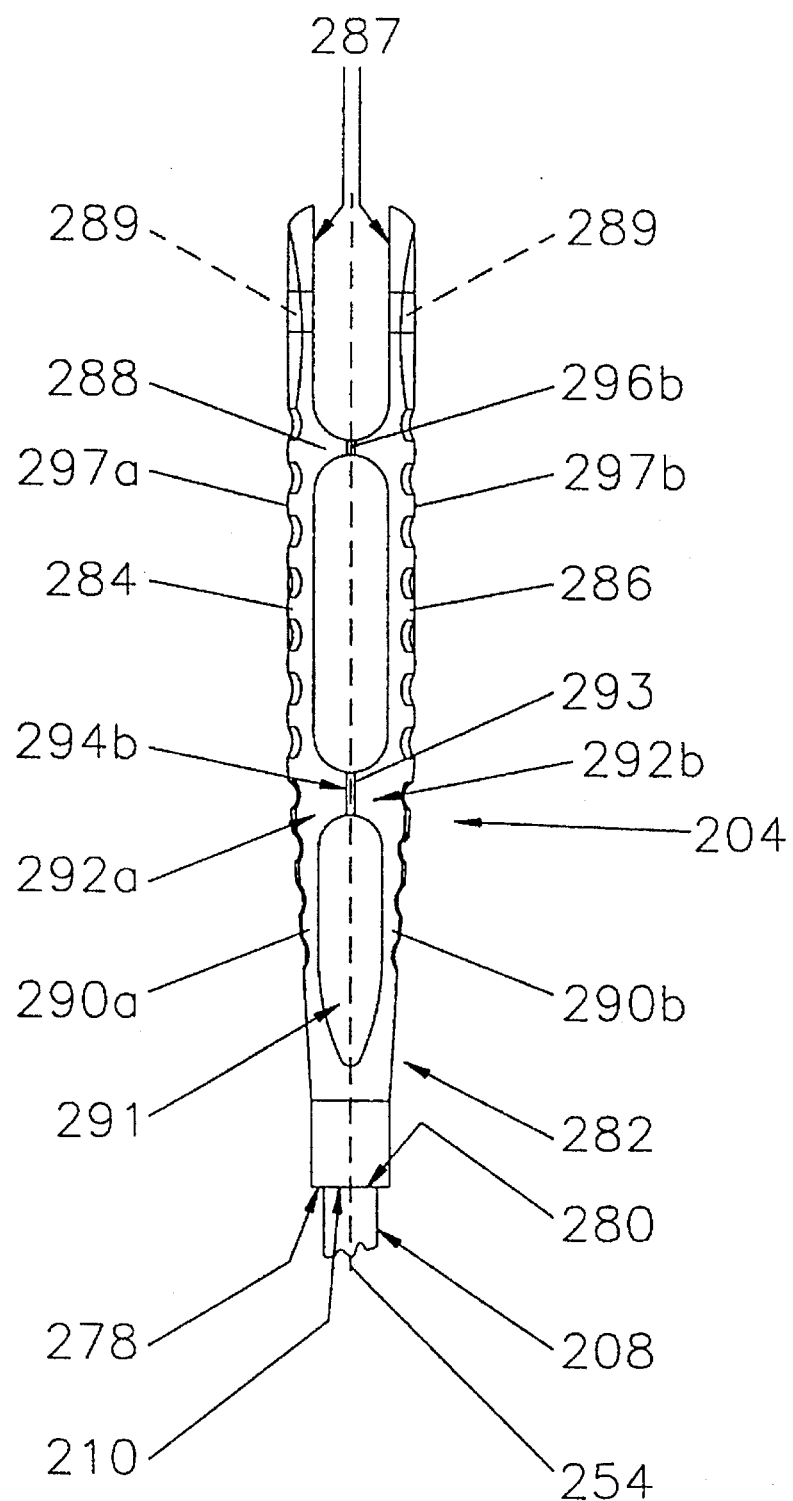
FIG. 8 is a side view partially cut away of the handle shown in FIG. 5, wherein the handle has been rotated 90° about its longitudinal axis.
Figure 9:
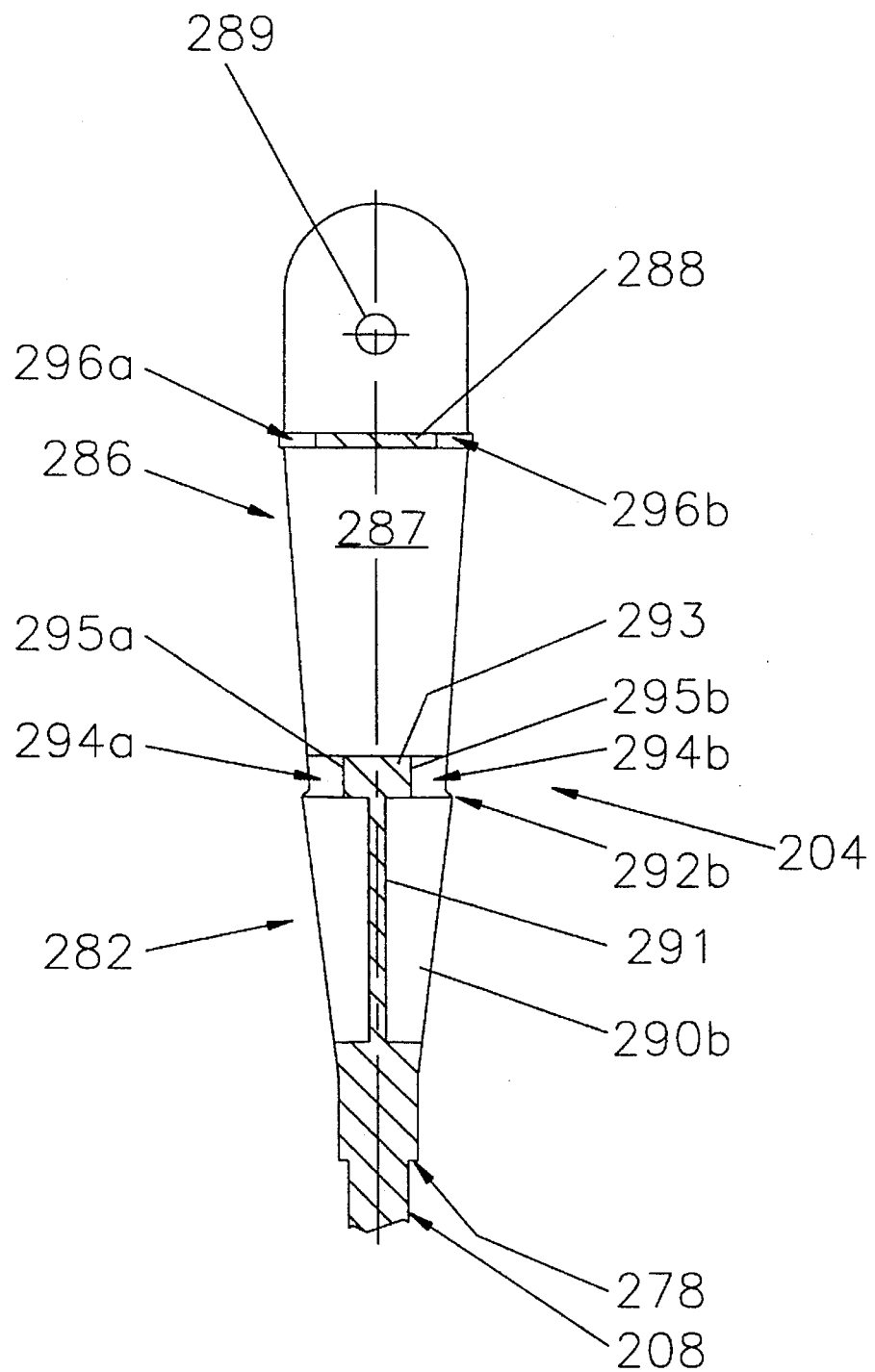
FIG. 9 is a sectional side view of the handle shown in FIG. 5 taken along the line A—A.

In summary, the preferred embodiment of the novel installation tool 202 includes a tubular element 206 (best seen in FIGS. 2–4); a shaft 208 having a handle 204 at its proximal end 210 (best seen in FIGS. 5, 8 and 9); and a bobbin-like member 402 (best seen in FIGS. 10–13). The tubular element 206 is adapted to receive and hold a co-axially oriented portion of suture anchor 102 in its distal end 212 (see FIG. 14). The shaft 208 is located in central lumen 214 of tubular element 206, and is movable between a first, retracted position and second, extended position (FIGS. 6 and 7).

Figure 2:
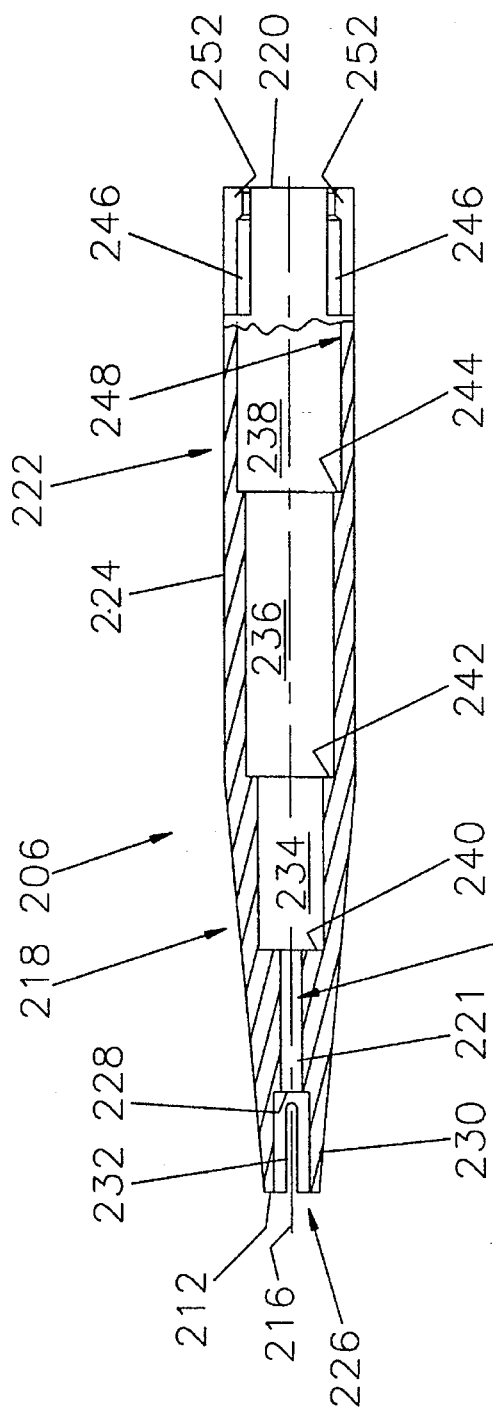
FIG. 2 is a side view in section of the tubular member of the installation tool shown in FIG. 1.
Figure 4:
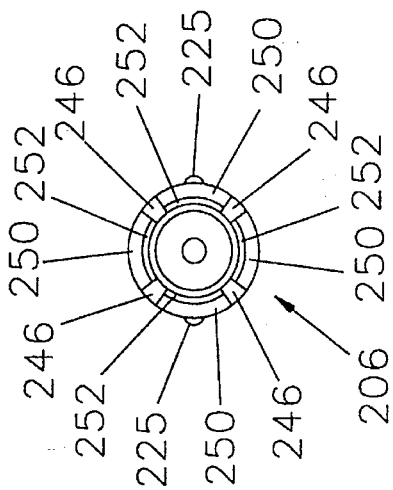
FIG. 4 is a proximal end view of the tubular member shown in FIG. 2.
Figure 3:
FIG. 3 is a distal end view of the tubular member shown in FIG. 2.

Turning now specifically to FIGS. 2 to 4, it will be seen that tubular element 206 is an elongate member having a longitudinal axis 216, a distal end 212, a distal portion 218 adjacent distal end 212, a proximal end 220, a proximal portion 222 adjacent proximal end 220, a central lumen 214 extending from the distal end 212 to proximal end 220, and an outer surface 224. Outer surface 224 defines at least one outwardly extending longitudinal rib 225. The distal end 212 has a cross-section transverse to longitudinal axis 216 which is somewhat larger than the transverse cross-section of hole 304 in bone 302 (see FIG. 1). Further, distal portion 218 of tubular member 206 is tapered so as to form a generally distally pointed configuration.

A first longitudinal counterbore 226 extends axially into distal end 212 of tubular element 206. The junction of portion 221 of central lumen 214 and first counterbore 226 defines a distally facing shoulder 228. The first counterbore 226 is sized to receive a co-axially oriented portion of body 104 of suture anchor 102 as generally described above.

The side wall 230 of first counterbore 226 defines a number of circumferentially spaced, longitudinal slots 232. The number and positioning of these slots is selected to correspond to the number and circumferential spacing of barbs 106 of anchor 102, plus the number and circumferential spacing of the free ends of suture 2 extending from attachment means 108 of anchor 102. In the embodiment shown, there are only two slots 232 because the barbs 106 are aligned with the bore 108 through which suture 2 extends.

Each slot 232 opens onto distal end 212 of tubular element 206. The slots 232 corresponding to the circumferential locations of barbs 106 of anchor 102 are aligned with the ribs 225, and are sized to accommodate the barbs when anchor 102 is co-axially inserted into first counterbore 226 so that its proximal end 112 abuts shoulder 228. Similarly, the slots 232 corresponding to the circumferential location of the free ends of suture 2 extending from attachment means 108 of anchor 102 are sized to allow those free ends to extend therethrough when anchor 102 is co-axially located within first counterbore 226 (see, for example, U.S. patent application Ser. No. 07/837,061).

Second, third and fourth counterbores, 234, 236 and 238, extend axially into proximal end 220 of tubular element 206. Second counterbore 234 is axially longer, and has a smaller transverse cross-section than counterbore 236. Similarly, counterbore 236 is axially longer, and has a smaller transverse cross-section than counterbore 238. Accordingly, the transverse cross-section of lumen 214 varies as it extends from proximal end 220 to distal end 212. Specifically, the transverse cross-section of lumen 214 through tubular element 206 varies from the size of counterbore 238 adjacent to proximal end 220, to the slightly smaller size of counterbore 236, to the smaller size of counterbore 234, to the still smaller size of lumen portion 221, and then to the slightly larger size of counterbore 226 adjacent distal end 212.

A proximally facing shoulder 240 is located at the junction of lumen portion 221 and second counterbore 234. Another proximally facing shoulder 242 is located at the junction of second and third counterbores 234 and 236. Still another proximally facing shoulder 244 is located at the junction of third and fourth counterbores 236 and 238. In addition, a plurality of longitudinal slots 246 extend through side wall 248 of fourth counterbore 238 so as to form proximally extending, longitudinal arms, generally indicated at 250. In the particular embodiment shown, there are four slots 246 forming four arms 250 (see FIG. 4).

Rib-like projections 252 extend inwardly from side wall 248 of fourth counterbore 238 adjacent and substantially parallel to proximal end 220 of tubular element 206. Projections 252 are located respectively along side wall 248 of fourth counterbore 238 between adjacent edges of longitudinal slots 246.

Figure 5:
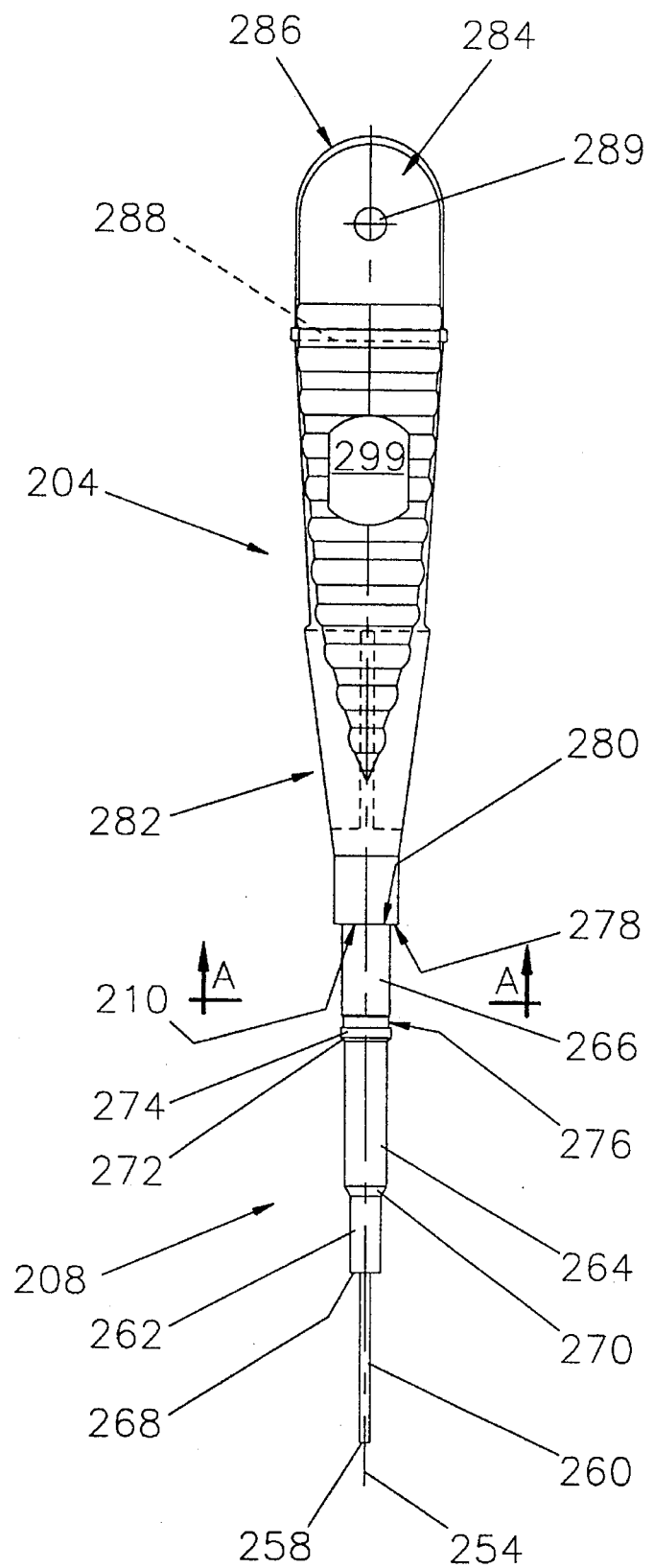
FIG. 5 is a side view of the shaft/handle of the installation tool shown in FIG. 1.
Figure 6:
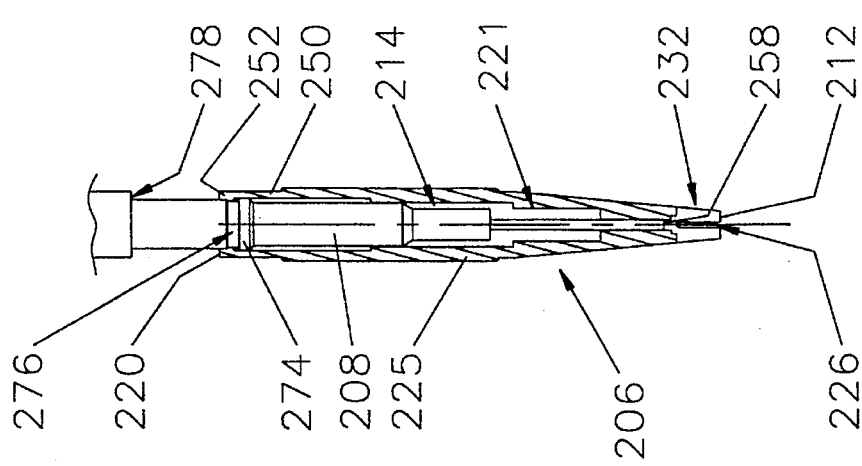
FIG. 6 is a side view, in partial section and partially cut away, showing the tubular element of FIG. 2 and the shaft of FIG. 5 in a first, retracted position relative to one another.

FIGS. 5–7 show a solid, substantially rigid shaft 208 having a longitudinal axis 254, a proximal end 210, a distal end 258, and a handle 204 extending proximally from proximal end 210. The cross-section of shaft 208 perpendicular to longitudinal axis 254 varies along the length of shaft 208 from a small cross-section portion 260 adjacent distal end 258, to a slightly larger cross-section portion 262, to a larger cross-section portion 264, to a still larger cross-section portion 266 adjacent proximal end 210. The cross-section of portion 260 is selected to be smaller than the transverse cross-section of hole 304 in bone 302 (FIG. 1). Also, the axial length of portion 260 is selected to exceed the longitudinal distance between shoulder 240 and distal end 212 of tubular element 206. The amount by which the axial length of portion 260 of shaft 208 exceeds this distance is selected to equal the depth to which proximal end 112 of body 104 is to be inserted into hole 304 in bone 302.

A distally facing shoulder 268 is located at the junction of portions 260 and 262. Another distally facing shoulder 270 is located at the junction of portions 262 and 264. Still another distally facing shoulder 272 is located at the junction of portions 264 and 266. Shoulder 268 is disposed substantially perpendicularly to longitudinal axis 254. Shoulders 270 and 272, on the other hand, each taper inwardly and distally toward longitudinal axis 254. Also, adjacent the joinder of portion 264 to portion 266, a rib-like projection 274 extends outwardly from, and circumferentially around, portion 266. A groove 276 extends circumferentially into and around shaft 208 substantially immediately proximally of rib-like projection 274.

The lengths and cross-sections of the various portions of shaft 208 and the various bores and counterbores of tubular element 206 are selected relative to each other so that the tubular element may be telescoped in sliding relationship onto the outer surface of the shaft. This relationship of shaft 208 and tubular element 206 is retained by a snap-fit engagement of the rib-like projections 252 carried by the proximally extending arms 250 over the outwardly extending rib-like projection 274, and into the circumferential groove 276. (See FIGS. 6 and 7).

Shaft 208, therefore, is movable longitudinally relative to tubular element 206 between a first, retracted position (FIG. 6) and a second, extended position (FIG. 7). In the first, retracted position, the rib-like projections 252 carried by proximally extending arms 250 are snap-fit over rib-like projection 274 and into circumferential groove 276. Also, distal end 258 of shaft 208 resides within the smallest cross-sectional portion 221 of lumen 214. As noted above, portion 221 of lumen 214 is located immediately proximally of first counterbore 226.

In the second, extended position, proximal end 220 of tubular element 206 is located in abutting relation with a distally facing shoulder 278 formed at the junction of proximal end 210 of shaft 208 and handle 204. In this position, distal end 258 of shaft 208 extends a preselected distance beyond distal end 212 of tubular element 206.

Figure 14:
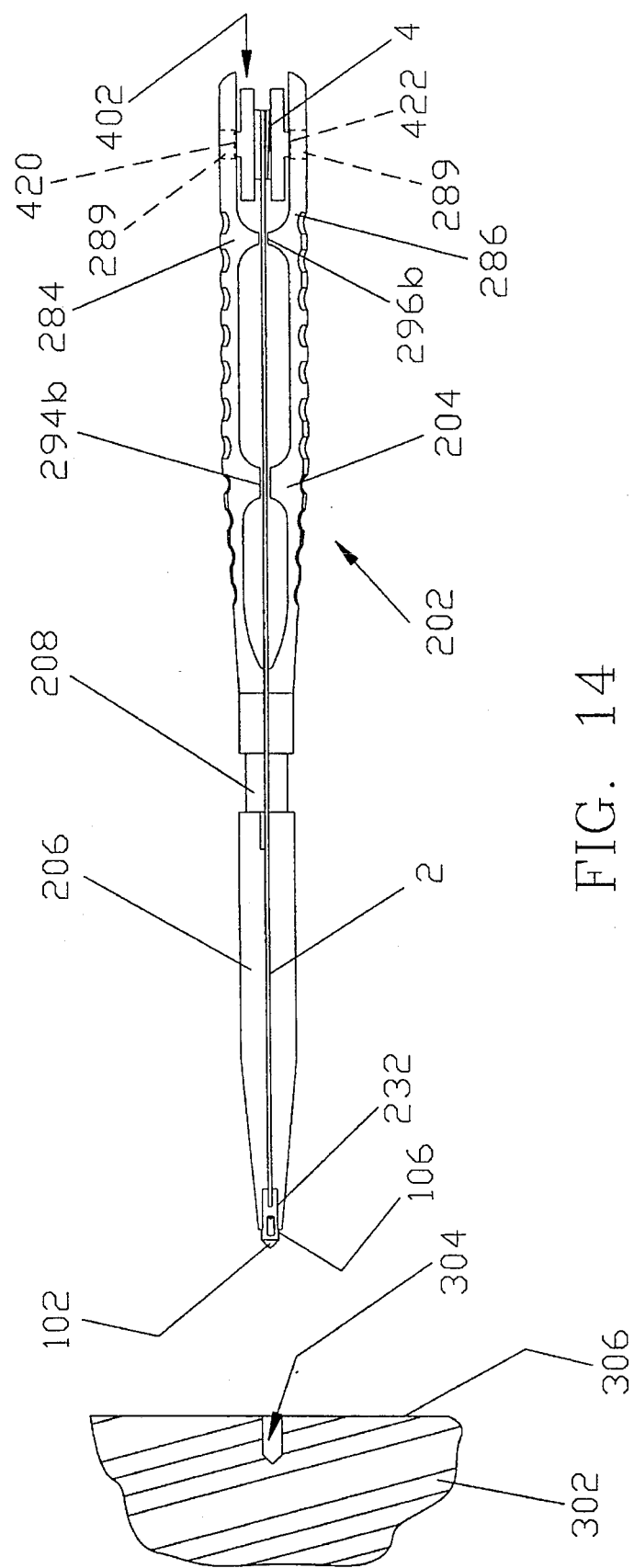
FIG. 14 is a side view in partial section showing (a) the installation tool of FIG. 1 in its first retracted configuration with the bobbin-like element in engagement with the handle, and (b) a suture anchor having its proximal portion engaging the distal end of the installation tool.
Figure 15:
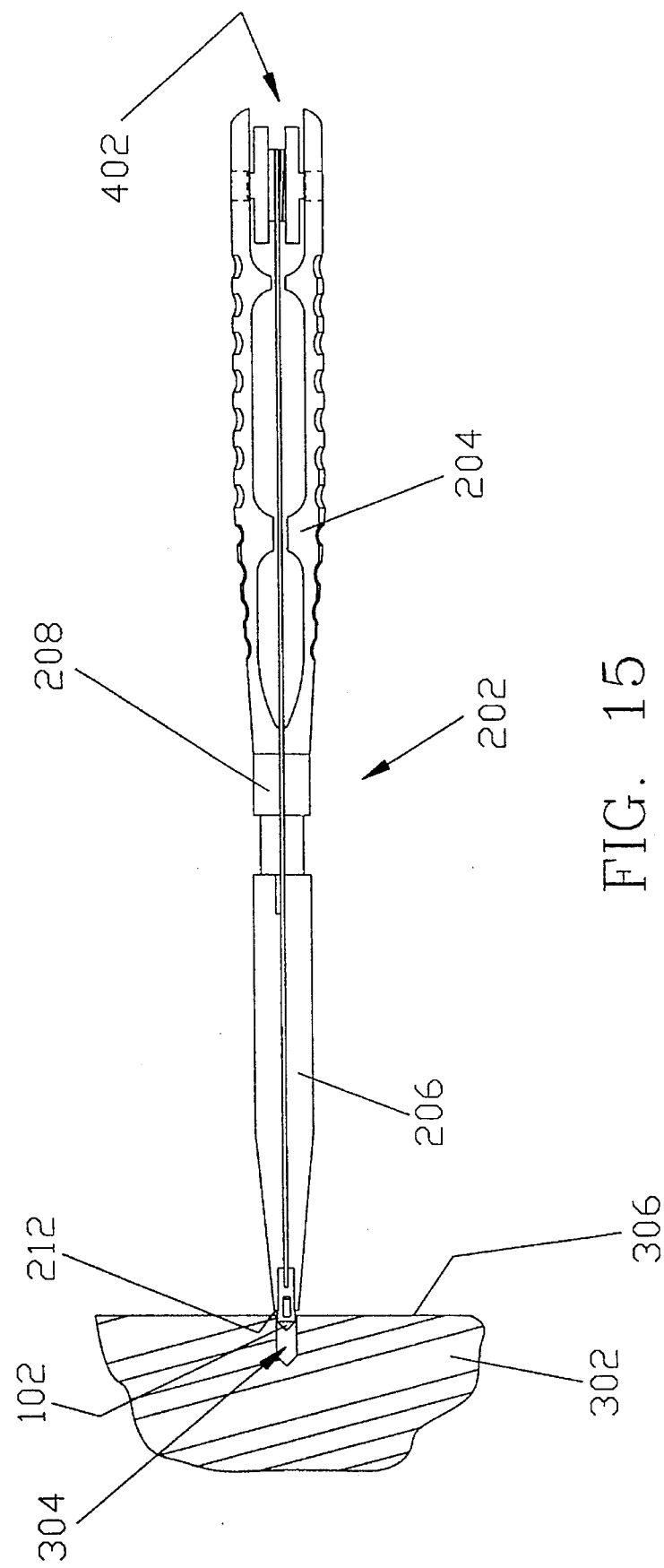
FIG. 15 is a side view in partial section showing (a) the installation tool of FIG. 1 in its first, retracted configuration, with the bobbin-like element in engagement with the handle, and (b) a suture anchor having its proximal portion engaging the distal end of the installation tool and its distal end engaging the proximal end of a hole formed in a bone.

Accordingly, as will be described in further detail below, with the tool in its first, retracted position, an anchor 102 may be co-axially located and held in the first counterbore 226 (see FIG. 14). In this configuration, the anchor may be conveniently carried to the target hole by the installation tool, as generally shown in FIG. 15. Also in this configuration, barbs 106 of anchor 102 are held in alignment with ribs 225 on the outer surface of tubular member 206 by slots 232. This allows the surgeon to easily align the barbs in a desired relationship to the hole 304 by simply twisting tubular member 206 relative to shaft 208. Such ease of barb alignment avoids the need to twist the entire tool in order to appropriately align the barbs with the hole. Such alignment can be very important. This is because in many surgical procedures utilizing suture anchors, care must be taken to avoid barb penetration of a joint or other sensitive area either during the insertion process or upon the "setting" of the barbs.

Figure 16:
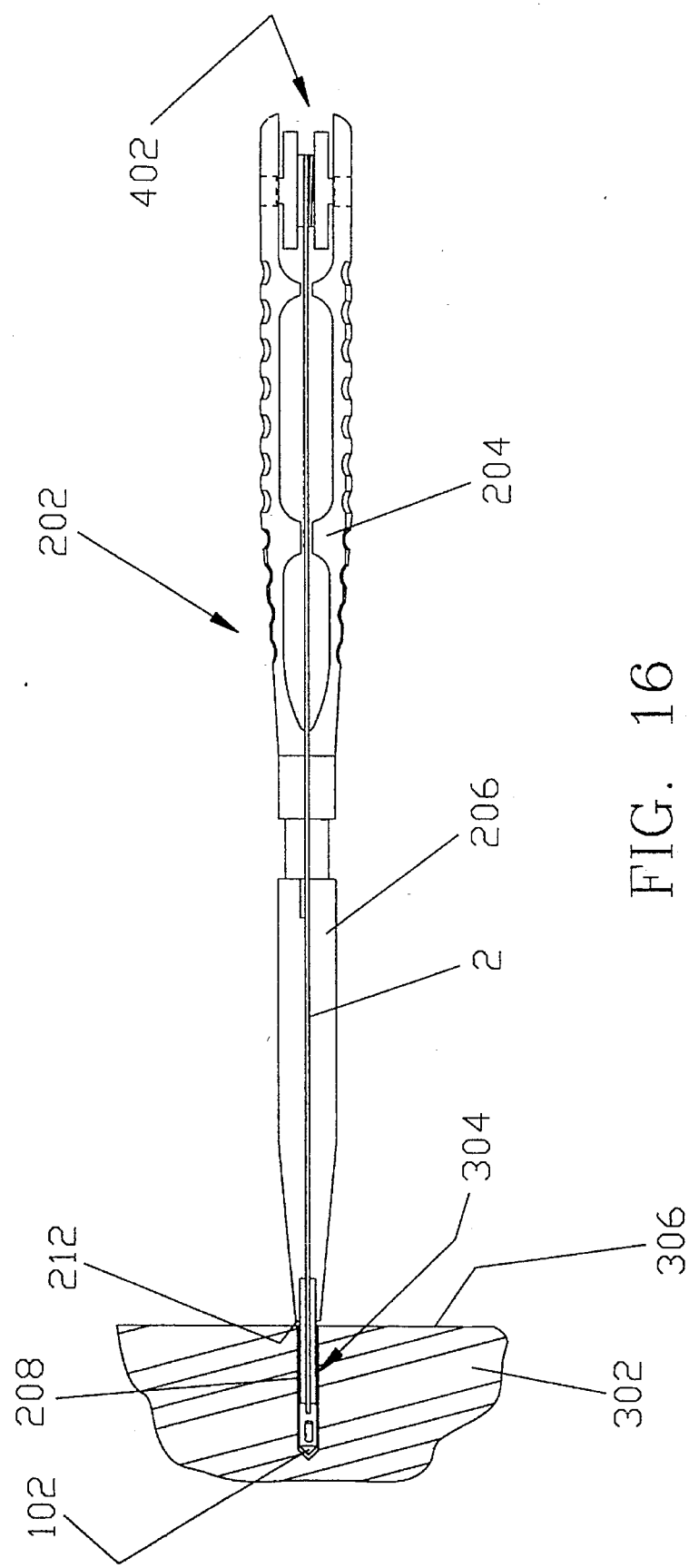
FIG. 16 is a side view similar to FIG. 15, but showing the installation tool in its second, extended configuration, and the suture anchor disposed within the hole in the bone.
Figure 17:
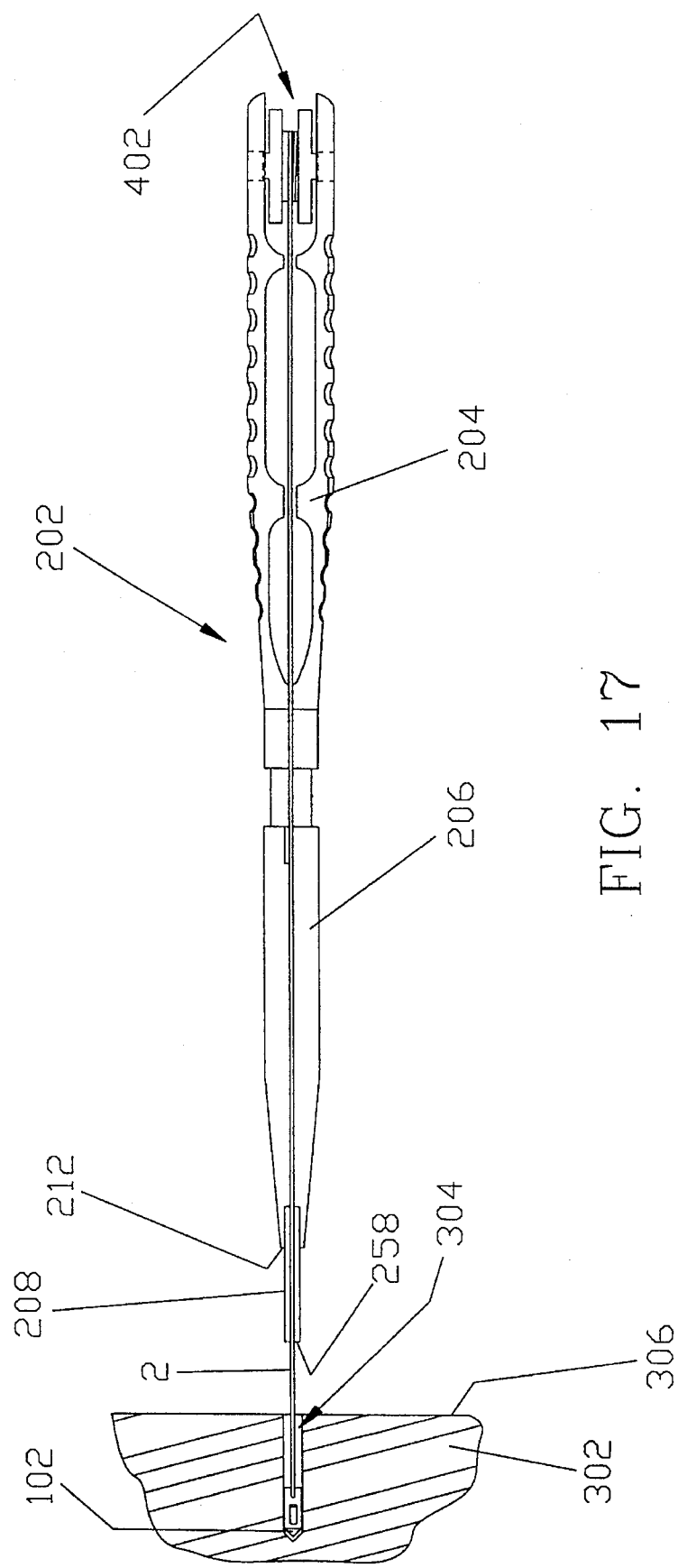
FIG. 17 is a side view similar to FIG. 16, but showing the installation tool removed from the hole and the anchor disposed at a desired position in the hole.
Figure 18:
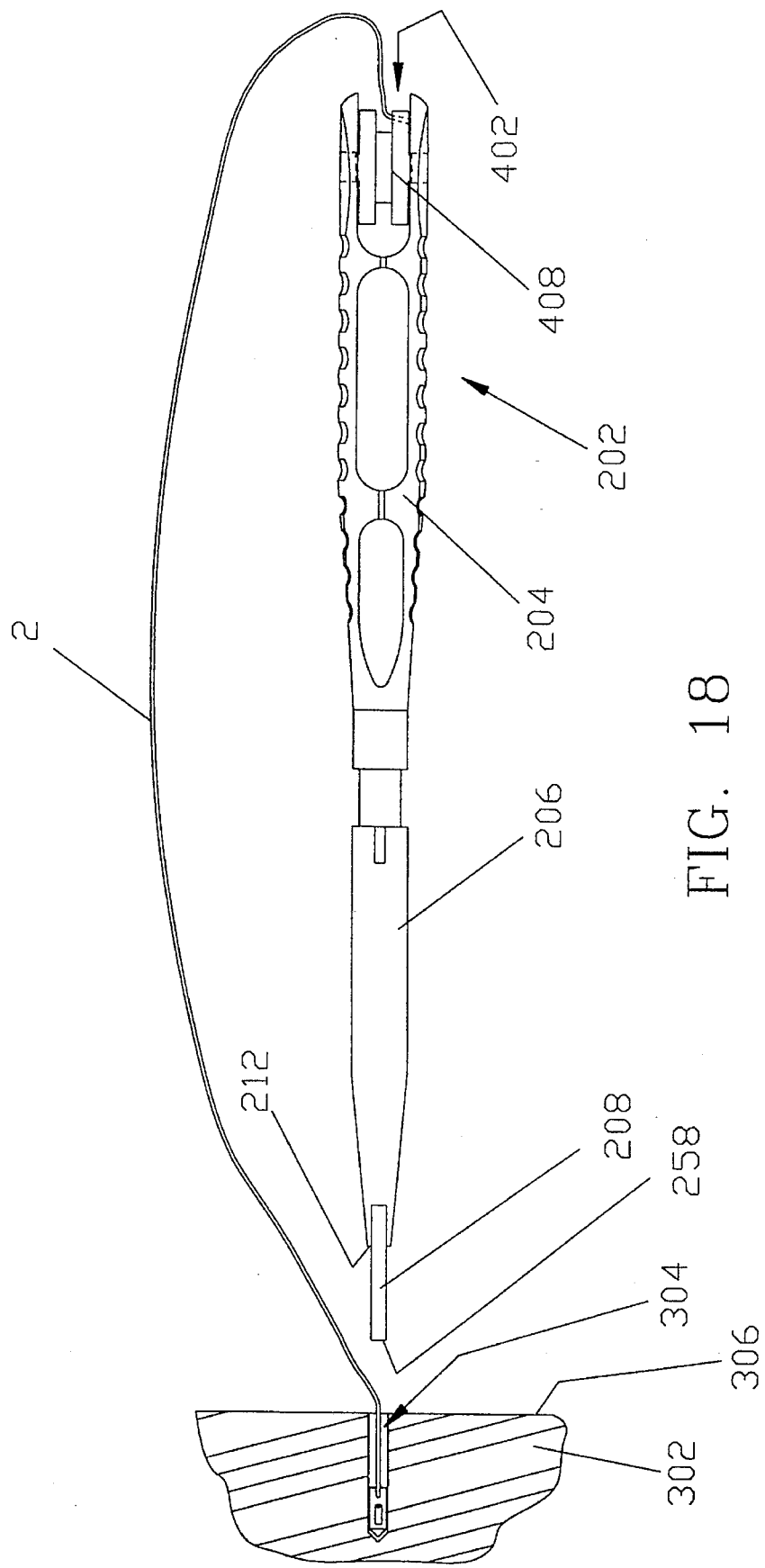
FIG. 18 is a side view similar to FIG. 17, but showing the suture disengaged from the continuous groove of the bobbin-like member.

Thereafter, while holding the distal end 212 of tubular element 206 against surface 306 of bone 302, the anchor 102 may be driven into the target hole 304 to its desired anchoring position by distal end 258 of shaft 208 (FIG. 16). This is accomplished by forcing the rib-like projections 252 carried by proximally facing arms 250 of tubular element 206 out of engagement with circumferential groove 276, and proximally along shaft portion 266 to shoulder 278.

The handle 204 (best seen in FIGS. 5, 8 and 9) comprises a distal end 280, a distal portion 282 adjacent the distal end 280, a pair of opposing substantially identical arms 284, 286 and a wall portion 288.

Handle 204 extends proximally from proximal end 210 of shaft 208. A distally facing shoulder 278 is formed by distal end 280 adjacent the joinder of shaft 208 to handle 204.

Distal portion 282 may be a solid structure. In the preferred embodiment shown in FIGS. 5, 8 and 9, however, it will be seen that distal portion 282 of handle 204 comprises a pair of opposing arms 290a, 290b connected by a longitudinally extending wall 291. Specifically, arms 290a and 290b taper outwardly from distal end 280 to outer, wide ends 292a and 292b. Longitudinal wall 291 extends proximally from distal end 280 to end wall 293. End wall 293 is located in a plane perpendicular to longitudinal axis 254, and connects the central portions of outer, wide ends 292a and 292b of arms 290a and 290b. Notches 294a and 294b are located adjacent the free side edges 295a and 295b of wall 293. The formation of distal portion 282 in this configuration lightens the handle, and facilitates the passage of the suture 2 from the anchor 102 through the notches 294a and/or 294b to the retention means 402.

Arms 284 and 286 extend proximally from wide ends 292a and 292b of distal portion 282 respectively. Each arm 284, 286 defines a substantially planar, inwardly facing surface 287 and a bore 289. The bores 289 are aligned with one another on a common axis perpendicular to the longitudinal axis 254, and are located in the proximal portion of arms 284 and 286 respectively.

Wall portion 288 connects arms 284 and 286 at a predetermined location along their longitudinal lengths approximately one-half to two-thirds of the longitudinal distance between wall 293 and the proximal end of handle 204. Specifically, wall portion 288 is oriented substantially perpendicular to both longitudinal axis 254 and planar surfaces 287. In addition, wall portion 288 and arms 284 and 286 together define side notches 296a and 296b. Notches 296a and 296b are respectively longitudinally aligned with notches 294a and 294b to facilitate the passage of suture 2 along handle 204.

Figure 19:
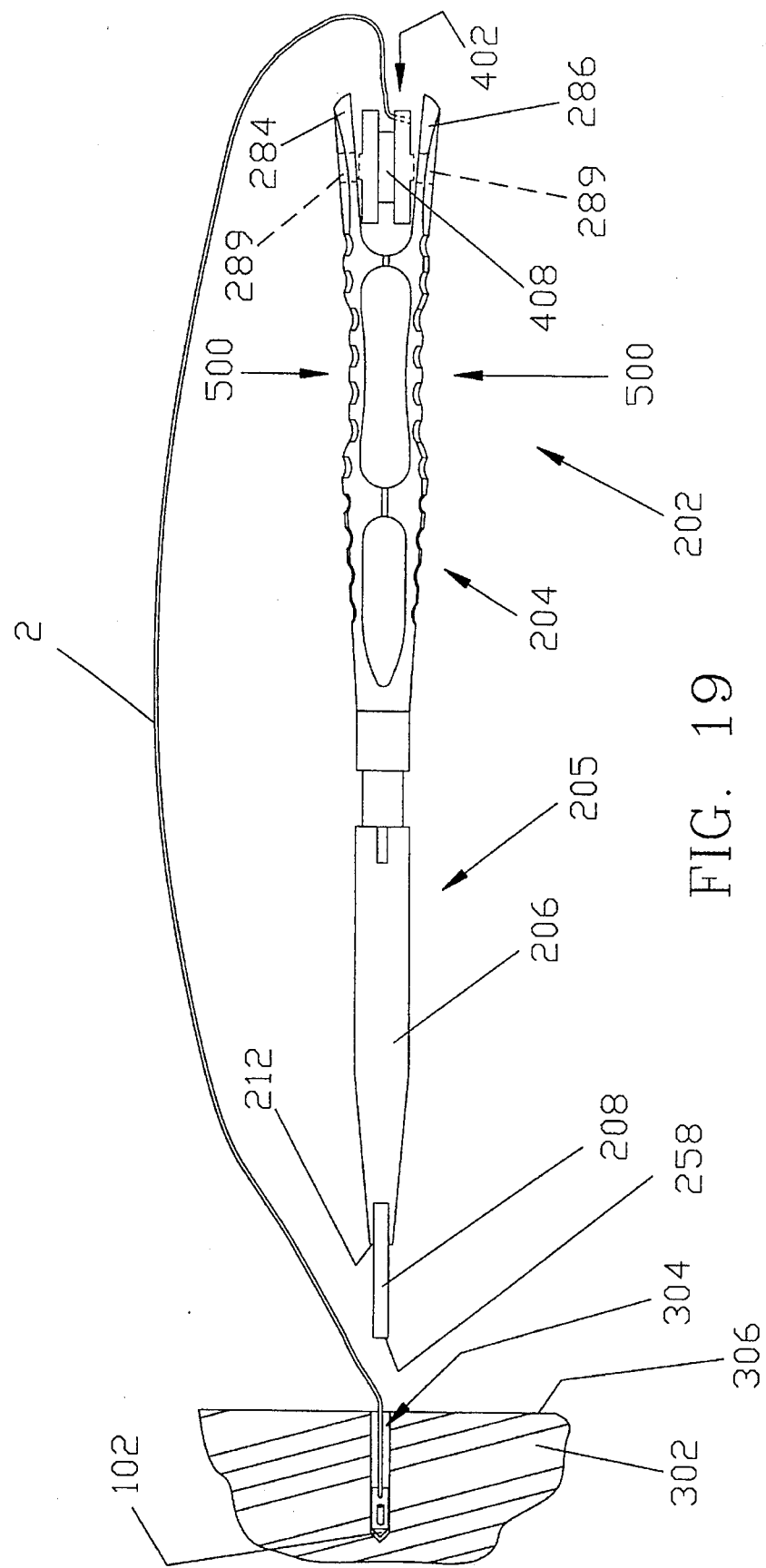
FIG. 19 is a side view showing the anchor disposed at a desired position in the hole, the suture disengaged from the continuous groove of the bobbin-like member, and the bobbin-like member released from the proximal portion of the handle.
Figure 20:
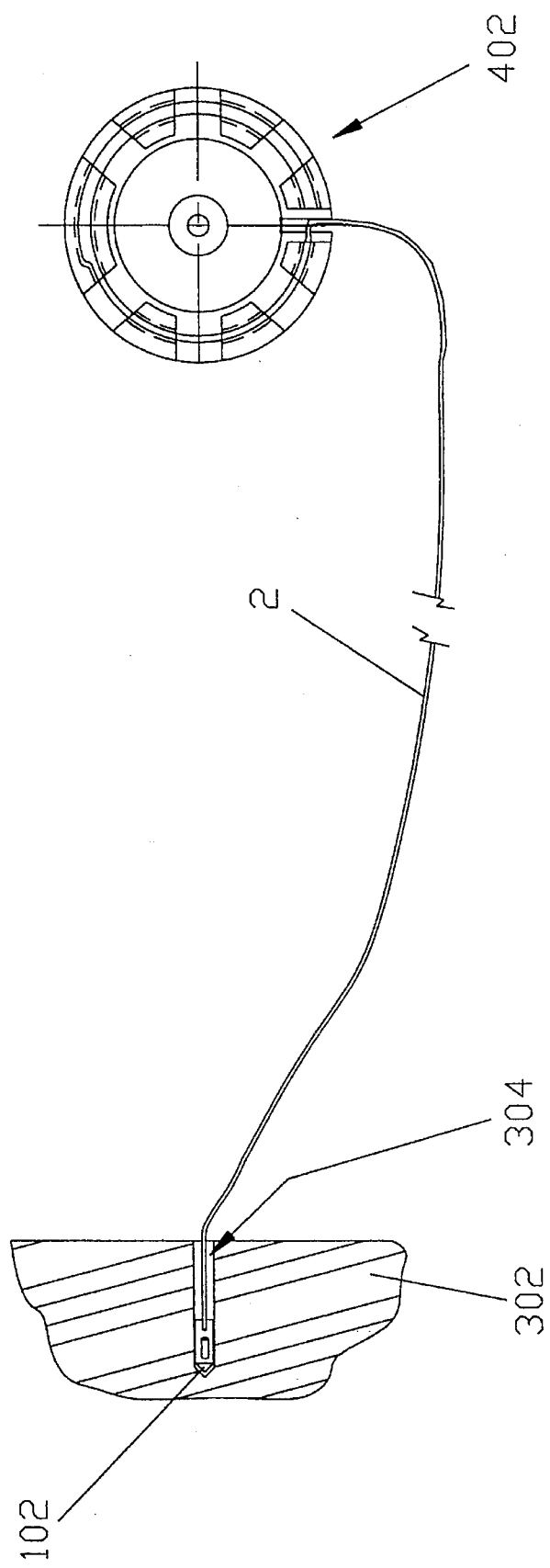
FIG. 20 is a side view showing the anchor disposed at a desired position in the hole, the suture disengaged from the continuous groove of the bobbin-like member, and the bobbin-like member totally disengaged from the tool and ready for the free ends of the suture (and any needles associated therewith) to be removed therefrom.

The outer surfaces 297a and 297b of arms 284 and 286 may be ribbed, scored or otherwise textured so as to assure that an individual using the device may firmly grasp and manipulate the same. If desired, flattened pressure receiving pads 299 (see FIG. 5) may be provided on outer surfaces 297a and 297b between connecting wall portion 288 and distal portion 282. The location of pads 299 is important because the operation of the device contemplates that inwardly directed pressure (see arrows 500, FIG. 19) will be applied to the outer surface of the portions of the arms 284 and 286 residing between distal portion 282 and connecting wall 288. Such inward pressure (i) bends the portions of arms 284 and 286 located between distal portion 282 and wall portion 288 inwardly; (ii) pivots the portions of arms 284 and 286 located proximally of wall 288 about the edges thereof attached to arms 284 and 286; and (iii) moves bores 289 away from each other (see FIG. 19).

The bobbin-like member 402 (best seen in FIGS. 10–13) includes a pair of opposing, generally cylindrical, side portions 404, 406 connected in parallel, spaced relation by axle portion 408. The bobbin-like member 402, therefore, defines a centered, continuous groove 410 between the opposing side portions 404, 406.

Each side portion 404, 406 defines a peripheral edge, 412, 414 respectively, and an outwardly facing, circular end surface 416, 418 respectively. An axially oriented, substantially cylindrical projection 420, 422 extends outwardly from each end surface 416, 418, respectively. In addition, a plurality of arcuate projections, generally indicated at 424, 426, extend outwardly from end surfaces 416, 418 respectively, parallel to, but a distance shorter than, the axial projections 420, 422 therefrom. Arcuate projections 424, 426 are located adjacent to the peripheral edges 412, 414 of their associated side portions 404, 406. They are also spaced from the axial projection 420 or 422 of their associated side portion, and circumferentially spaced one from the other.

Each of the arcuate projections 424, 426 defines an outer surface, generally indicated at 428, 430 respectively, and an arc-shaped slot, generally indicated at 432, 434 respectively. The outer surfaces 428, 430 of arcuate projections 424, 426 are located in common planes 436, 438 respectively. Planes 436 and 438 are spaced respectively outwardly from, and parallel to, an adjacent end surface of one of the side portions.

The slots 432, 434 each extend through their associated arcuate projection in concentric spaced relation to the peripheral edge of their associated side portion, and inwardly from the outer surface of the projection through the associated side portion to the continuous groove 410. Together, these arc-shaped slots define broken, circular grooves 440, 442 which are spaced radially inwardly of the peripheral edge of their respective associated side portion.

Grooves 440, 442 are adapted to releasably receive and hold a curved surgical needle 444 and/or a free end 4 of suture 2 (as shown in phantom in FIG. 11). Accordingly, grooves 440 and 442 define portions (representatively shown at 440a in FIG. 11) having a width slightly larger than the diameter of suture 2, and portions (representatively shown at 440b in FIG. 11) having widths slightly larger than the diameter of needle 444. Further, a selected one of the arcuate projections 424 and 426 (designated by the numbers 424a and 426a) extends along a greater arc than the remainder of the arcuate projections extending from its associated side portion. Arcuate projections 424a and 426a define the location of the change in diameter of broken grooves 440 and 442 respectively. Accordingly, they are designed to releasably hold both a portion of the suture 2 and needle 444 attached to the free end 4 of suture 2.

Still further, at least one of the side portions 404, 406 defines a notch 446 (see FIG. 11) extending into its peripheral edge between a selected pair of the arcuate projections. Notch 446 opens into both the continuous groove 410 and the end surface of its associated side portion.

The bobbin-like member 402, therefore, is adapted to hold a portion of a length of suture 2 wrapped around the axle 408 in continuous groove 410. Another portion of that length of suture 2 extends from continuous groove 410 to attachment means 108 of anchor 102. Still another portion of that length of suture 2 extends from continuous groove 410 through notch 446 and portion 440a of groove 440 to surgical needle 444 which is releasably located in portion 440b of broken groove 440 (as shown in phantom in FIG. 11). The needle 444 is removable from the groove 440 by inserting a needle grasping device (not shown) into one of the spaces between the arcuate projections. Such a grasping device may engage the portion of a needle extending through that space. Thereafter, the exertion of an outwardly directed axial force on the grasping means will withdraw the needle from the broken groove defined by the arcuate projections. If desired, a curved surgical needle and/or free end of suture may be positioned in each of the grooves 440 and 442, or in only one of the grooves. In the preferred embodiment of the invention, surgical needles are disposed in both of the grooves 440, 442.

Figure 12:
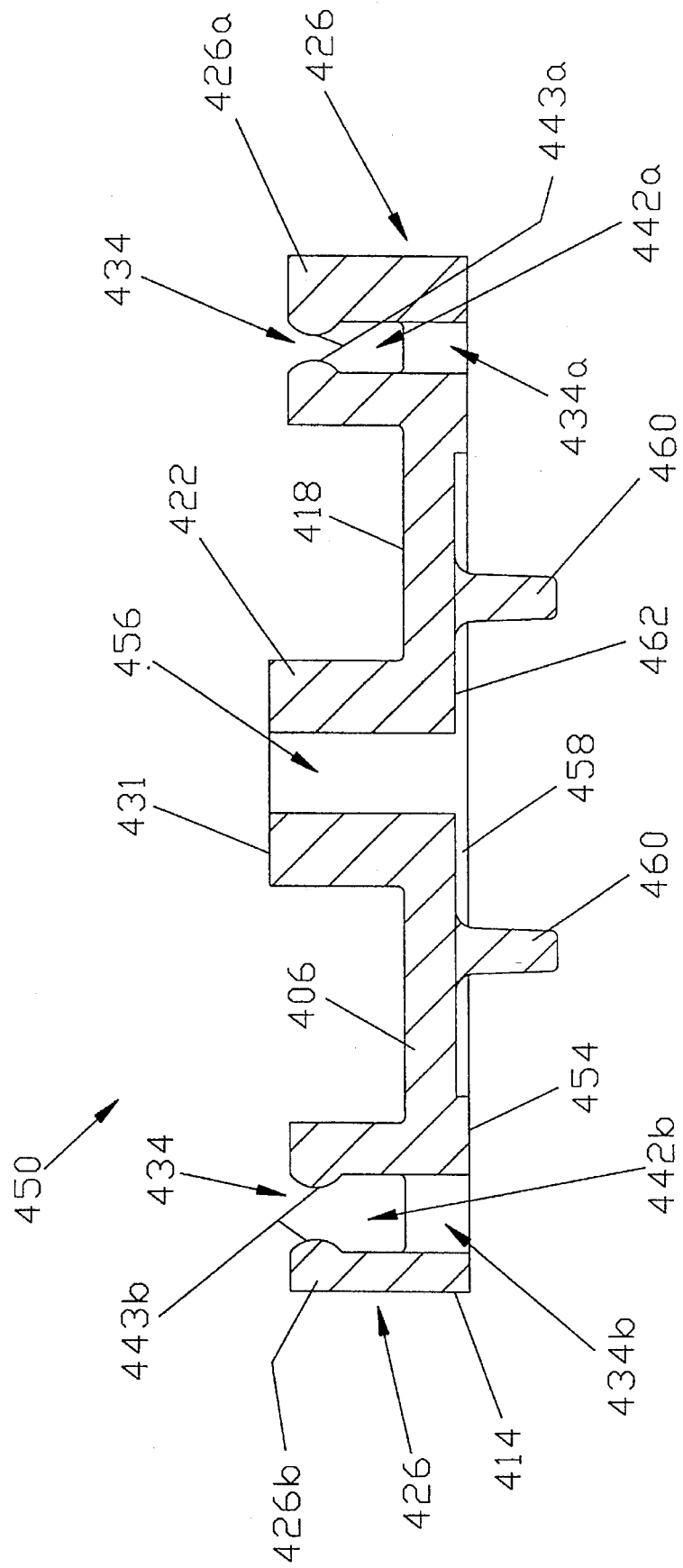
FIG. 12 is a sectional side view of the right hand portion of the bobbin-like member shown in FIG. 10 taken along the line B—B shown in FIG. 11.
Figure 13:
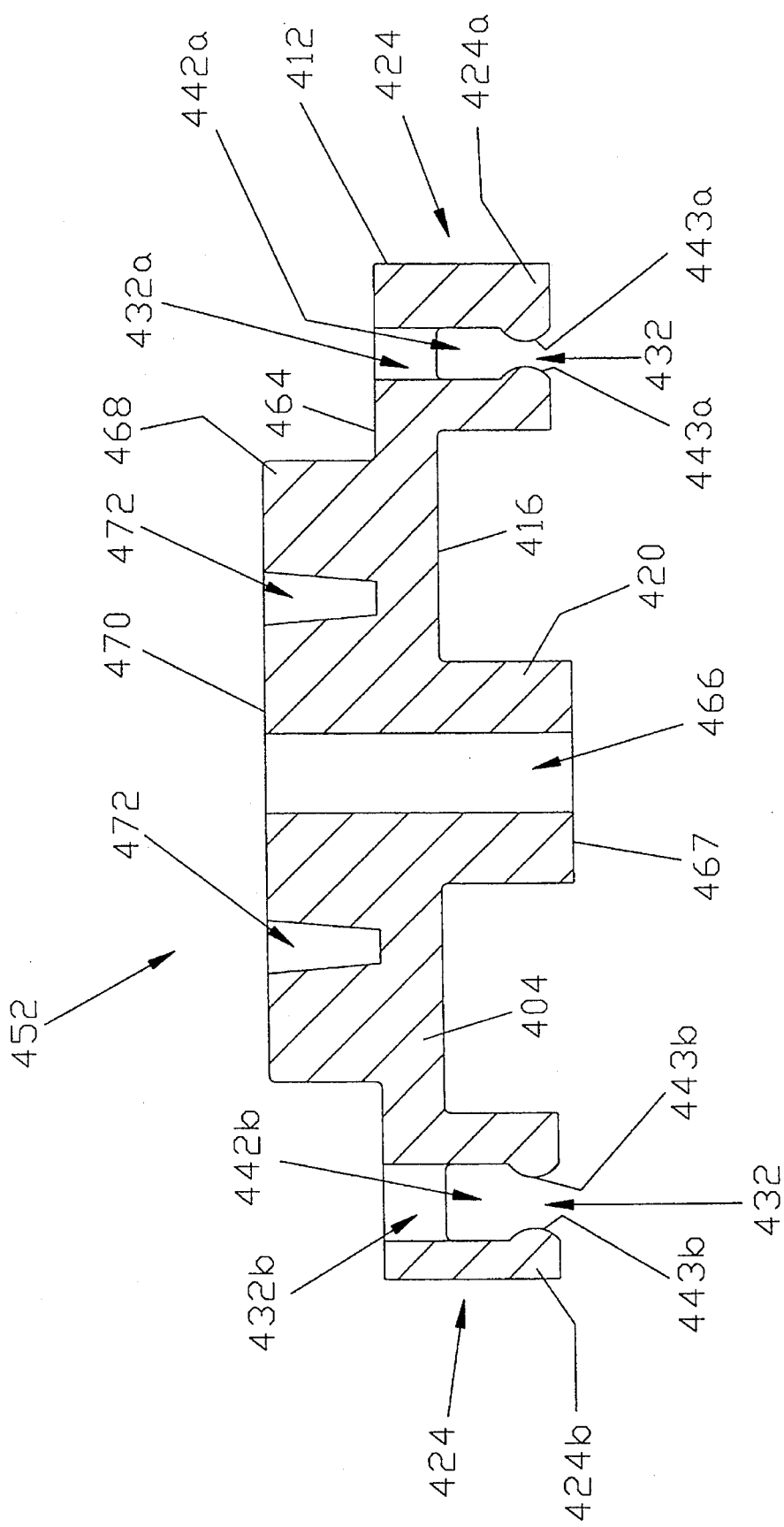
FIG. 13 is a sectional side view of the left hand portion of the bobbin-like member shown in FIG. 10 taken along the line C—C shown in FIG. 11.

It is to be understood that bobbin-like member 402 may be integrally formed as a single piece by molding, machining or some other process. In the preferred embodiment, however, bobbin-like member 402 is formed in two (2) pieces 450 and 452, as shown in FIGS. 12 and 13. Pieces 450 and 452 are thereafter joined to form the completed bobbin-like member (see phantom lines in FIG. 10). Specifically, FIG. 12 shows right hand piece 450 of the bobbin-like member 402 shown in FIG. 10, and FIG. 13 shows left hand piece 452 of bobbin-like member 402 shown in FIG. 10. FIGS. 11 and 12 are sectional views taken along the lines B—B and C—C respectively of FIG. 11 so as to show the internal structure of slots 432 and 434 in addition to the structure utilized to join pieces 450 and 452.

As particularly shown in FIG. 12, piece 450 includes side portion 406 having outer surface 418 and an inner surface 454. The cylindrical projection 422 extends outwardly from outer surface 418 and defines a central bore 456 extending from its outer surface 431 to inner surface 454 of the side portion 406. The arcuate projections 426 extend outwardly from outer surface 418 adjacent peripheral edge 414 and define the slots 434. Specifically, arcuate projections 426a each define a slot 434a forming the small width groove 442a and arcuate projections 426b each define a slot 434b forming the large width groove 442b. In addition, small retaining lips 443a and 443b may be provided adjacent to the openings of slots 434a and 434b into the outer surface of arcuate projections 426a and 426b. The extension of slots 434a and 434b through the arcuate projections parallel to the projection 422 facilitates the removal of suture and/or needles disposed in the broken groove by allowing the sides thereof to spread apart to thereby permit the passage of suture or a needle inwardly past the retaining lips 443a and 443b.

A centered, circular recessed area 458 of substantially uniform depth is formed in inner surface 454. Further, at least two, substantially equally circumferentially spaced fingers 460 extend perpendicularly inwardly from base 462 of recessed area 458. In the embodiment shown, fingers 460 extend inwardly opposite the circular space between arcuate projections 426a and 426b and cylindrical projection 422 from outer end surface 418.

Piece 452, on the other hand, is shown in FIG. 13. Piece 452 includes side portion 404 having outer surface 416 and an inner surface 464. The cylindrical projection 420 extends outwardly from outer surface 416 and defines a central bore 466 extending from its outer surface 467 perpendicularly through piece 452. The arcuate projections 424 extend outwardly from the outer surface 416 adjacent the peripheral edge 412 and define the slots 432. Specifically, arcuate projections 424a each define a slot 432a forming the small width groove 442a and arcuate projections 424b each define a slot 432b forming a large width groove 442b. In addition, small retaining lips 443a may be provided adjacent the opening of slots 432 into arcuate projections 424a and small retaining lips 443b may be provided adjacent the openings of slots 432 into arcuate projections 424b. Again, the extension of the slots through the piece facilitates the insertion of a suture or needle into the broken groove by allowing the outer side edges of the slots to spread apart.

A centered, cylindrical projection 468 extends perpendicularly inwardly from inner surface 464 to an inner end surface 470. Projection 468 defines cavities 472 extending into its end surface 470 which are sized and spaced to receive the fingers 460 of piece 450. Further, bore 466 extends axially through projection 468.

To assemble the bobbin-like member 402, the bore 456 of piece 450 is aligned with the bore 466 of piece 452, and the fingers 460 of piece 450 are aligned with the cavities 472 of piece 452. The pieces 450 and 452 are then moved toward each other such that the fingers 460 engage the cavities 472 in a pressed-fit or snap-fit relationship. At the same time, inner surface 470 enters recessed area 458 so as to abut base 462. It will, of course, be understood by those skilled in the art that more fingers and associated cavities may be provided in the respective pieces, that the entire inner end of the projection 468 need not enter a corresponding recessed area in piece 450, and that other attachment alternatives for joining pieces 450 and 452 may be utilized without departure from the present invention in its broadest aspects.

The bobbin-like member 402 is also releasably and rotatably maintained between planar surfaces 287 of arms 284 and 286 of handle 204. This is accomplished by a snap-fit engagement of the outwardmost portions of axial projections 420, 422 with the bores 289. Bobbin-like member 402 may be disengaged from handle 204 by applying inwardly directed pressure to the portions of the arms 284 and 286 located between distal portion 282 of handle 204 and connecting wall 288. This pressure (i) bends the portions of the arms located between the distal portion of the handle and the connecting wall inwardly; (ii) pivots the portions of the arms located proximally of the connecting wall about the edges of the wall attached to the arms, and (iii) moves the bores away from each other. This frees the projections 420, 422 from bores 289, and allows the bobbin-like member 402 to be slid along the planar surfaces 287 until it is disengaged from the tool 204. Bobbin-like element 402 may also be rotatably mounted between the arms of the handle by reversing the procedure just described.

The method of attaching an object to a workpiece utilizing the device of the present invention will now be described with reference to FIGS. 14–20. Specifically, the method contemplates that an anchor suitable for mounting a portion of a cord-like element within a preformed hole in a workpiece will be provided. Similarly, it is contemplated that an installation tool including anchor positioning means such as the preferred embodiment of the invention described in detail above, or another alternative configuration suitable for use with the anchor selected, also will be provided. For convenience of reference, the anchor will be assumed to be a suture anchor and the workpiece will be assumed to be a piece of bone. It again will be understood, however, that this context of use is presented by way of example only, and not by way of limitation.

First, a length of suture including a curved, surgical needle attached to at least one of its free ends, if desired, is attached to the selected suture anchor. In the embodiments shown, this is accomplished by threading the suture 2 through bore 108 located substantially adjacent proximal end 112 of suture anchor 102. Preferably, one surgical needle is attached to both of the free suture ends. The needle(s) attached to the free end(s) 4 of suture 2 are then inserted into the groove(s) 440, 442 adjacent the end surface(s) 416, 418 of bobbin-like member 402. Thereafter, the free end(s) of suture 2 extending from the needles are drawn through notch(es) 446 in side portion(s) 404, 406 of bobbin-like member 402. Most of the length of suture extending from the inner side of notch 446 is then wrapped around axle 408 of bobbin-like member 402 within continuous groove 410.

The suture anchor 102 is then attached to the distal end of the selected insertion tool. In the preferred embodiment, this is accomplished by co-axially inserting the proximal portion of body 104 into the first counterbore 226 in tubular member 206 while the insertion tool's shaft 208 is in its first, retracted position relative to its tubular element 206. In this configuration, barbs 106 and suture 2 both extend through slots 232. The suture extending between the continuous groove 410 and the anchor 102 may then be drawn tight against the sides of the insertion tool by rotating bobbin-like member 402 about axial projections 420, 422 located in bores 289 (see FIG. 14).

The anchor then is conveyed to bone hole 304 so that its distal portion resides in the hole while its proximal portion remains in counterbore 226 adjacent distal end 212 of installation tool 202 (see FIG. 15).

Thereafter, the anchor 102 is driven to a desired position within bone hole 304. This is accomplished by engaging distal end 212 of tubular member 206 with the bone adjacent bone hole 304. Shaft 208 then is moved relative to the tubular member 206 from its first, retracted position to its second, extended position. This ejects anchor 102 from tubular element 206 and drives anchor 102 into bone hole 304 (see FIGS. 6, 7 and 16). Distal end 258 of shaft 208 is then removed from bone hole 304, leaving anchor 102 at its desired anchoring location (see FIG. 17). Typically, the tool 202 is also removed from the immediate vicinity of the bone hole at this stage. This movement of the tool causes the bobbin-like element to rotate on its axis and the suture to be unwrapped from the axle 408 (see FIG. 18).

At this point, the entire installation tool may be retained in the immediate vicinity of the surgical field until the suture ends and needle(s) held by the groove(s) 440 and/or 442 are required by the surgeon. Alternatively, bobbin-like member 402 may be disengaged from handle 204 by reversing the above-described insertion procedure. Specifically, radially inwardly directed pressure (see arrows 500) is exerted on pressure receiving pads 299 so as to spread the proximal ends of arms 284 and 286. This spreading of the arms 284 and 286 frees the outermost portions of projections 420, 422 of bobbin-like element 402 from bores 289 (see FIG. 19). In this alternative, positioning portion 205 and handle 204 of tool 202 may be removed from the vicinity of the surgical field, leaving only the suture and needle carrying bobbin-like element near the surgical site (see FIG. 20).

Thereafter, at the point in the surgical procedure at which the surgeon requires the free suture end and/or needle for use in attaching an object to the bone, he simply removes the free suture end and/or needle(s) from groove(s) 440 and/or 442. This is accomplished by inserting a needle grasping device (not shown) into a space between two adjacent arcuate projections, grasping the suture and/or needle extending through that space with the grasping device, and pulling the suture/needle from the groove.

Finally, bobbin-like member 402 is removed from the vicinity of the surgical field so as to allow unimpeded access to the surgical site for the connection of an object to the bone with the suture and needle(s).

Numerous variations, changes, alterations and modifications of the present invention will occur to those skilled in the art in view of the foregoing detailed description of a preferred embodiment thereof. For example, the anchor selected may be different from the anchor shown in the drawings and described above. Similarly, the anchor positioning means may be different from that shown in the drawings and described above. Accordingly, anchors and anchor positioning means similar to those shown in any of the patents or patent applications incorporated by reference herein could be utilized with the handle and releasable suture/needle retention means described herein without departure from the present invention in its broadest aspects.

Figure 21:
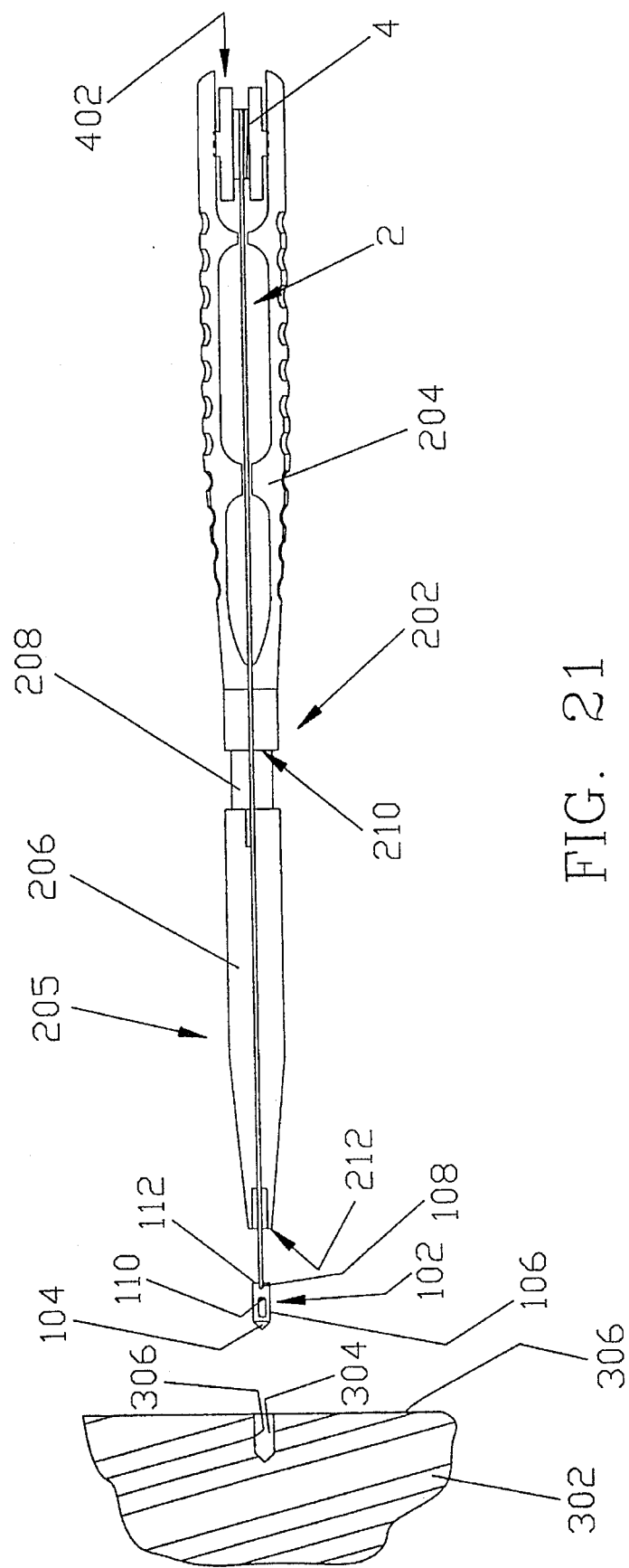
FIG. 21 is a view similar to FIG. 1 showing an alternative installation tool and bobbin-like member formed in accordance with the invention.

In addition, the elements providing the releasable attachment of the bobbin-like element 402 to the arms 284 and 286 could be reversed. Specifically, the bores 289 might be replaced with cylindrical projections extending inwardly from planar surfaces 287 of arms 284 and 286. In such a case, cylindrical projections 420, 422 from outer surfaces 416, 418 of bobbin-like member 402 would be replaced by cylindrical, blind bores adapted to rotatably receive the projections from the planar surfaces (see FIG. 21).

Further, it will be understood that arcuate projections need be provided on the outer end surface of only one of the side portions of the bobbin-like member in the case where only one needle is to be carried by the bobbin-like element 402.

Still further, it will be understood that the steps of the method described above are not to be considered as being limited to the particular sequence described. Specifically, once the suture has been attached to the anchor, the engagement of the anchor with the distal end of the installation tool, the location of the free suture end/needle in groove(s) 440 and/or 442, the wrapping of suture 2 around axle 408, and the disposition of the distal end of the anchor in the bone hole may be accomplished in any desired and/or convenient sequence. It is the intent of the invention that the tool, anchor, suture and retention means will be in their fully assembled configuration prior to the insertion of the anchor into the bone hole. It, however, is not the intent of the invention to limit the method disclosed and hereinafter claimed to any particular assembly sequence.

It should also be appreciated that suture 2 might have objects other than a needle or needles 444 attached to the free end(s) thereof. For example, the free end(s) of suture 2 might have other anchoring devices attached thereto, where such other anchoring devices might or might not be similar to the suture anchor 102 disclosed above. In such a case, bobbin-like element 402 can be appropriately modified in ways well known in the art so that bobbin-like element 402 can releasably hold such other anchoring devices in the same manner that it can hold needles 444.

The foregoing detailed description has been presented by way of illustration only. Accordingly, the scope of the invention is to be defined only by the limitations set forth in the appended claims.

What is claimed is:

1. A system for attaching an object to a workpiece comprising:

an anchoring device and an installation tool for deploying said anchoring device within a preformed hole in said workpiece;

said anchoring device having a portion of a length of cord-like material attached thereto, said cord-like material having at least one free end;

said installation tool comprising:
positioning means for locating said anchoring device at a predetermined depth within said hole, said positioning means including a handle;
retention means for releasably holding a portion of said length of cord-like material extending from said anchoring device and also releasably holding said free end of said cord-like material, said retention means being releasably attachable to said handle of said positioning means; and said cord-like material having a curved needle-like member attached to another one of its free ends, and wherein said retention means includes means for releasably holding said needle-like member.

2. A system according to claim 1 wherein said retention means comprises a bobbin-like element, said bobbin-like element comprising a transverse central axis, a pair of opposing side portions connected in parallel, aligned and spaced relation to one another by axle means centered on said transverse axis so as to define a continuous groove therebetween;

at least one of said side elements including a peripheral edge, an outwardly facing surface and a radial notch, said radial notch extending into said peripheral edge and communicating with said continuous groove and with said outwardly facing surface; and at least two arcuate projections extending outwardly from said outwardly facing surface of said at least one side portion, said arcuate projections being located in circumferentially spaced relation to each other substantially adjacent to said peripheral edge and defining at least one cord-like material/needle-like member retention groove; and each said side portion defining engagement means centered on said transverse axis and adapted to rotatably and releasably engage said handle;

whereby said cord-like material extending from said anchoring device may extend into said continuous groove, be wrapped around said axle and extend outwardly through said notch so as to allow said free end and said needle-like member to be located in said groove.

3. A system according to claim 2 wherein said handle comprises a pair of opposing proximally extending arms adapted to releasably hold said retention means.

4. A system according to claim 3 wherein said handle includes a longitudinal axis, a distal end, a distal portion adjacent said distal end, a proximal end and a proximal portion adjacent said proximal end, said proximal portion defining said arms and a wall portion, said arms each defining second engagement means adjacent said proximal end of said handle and an inwardly facing planar surface, each said second engagement means being centered on a common axis perpendicular to said longitudinal axis and being adapted to rotatably and releasably engage said engagement means of said bobbin-like element, and said wall portion connecting said planar surfaces substantially midway between said proximal end and said distal portion of said handle in a plane transverse to said handle.

5. A system according to claim 1 wherein said anchoring device comprises (a) a body having a longitudinal axis and a maximum cross-section transverse to said longitudinal axis, (b) at least one elastically deformable barb, each said barb extending from said body, rearwardly and outwardly to an outer end, said outer end being located radially outwardly of an axial projection of said maximum transverse cross-section of said body when said barb is in a nondeformed configuration, and (c) connection means for attaching said portion of said length of cord-like material to said body.

6. A method for attaching an object to a workpiece having a preformed hole therein comprising the steps of:

(a) providing an assembly comprising:
(i) an anchoring device adapted for fixed location within said hole;
(ii) a length of cord-like material, said length of cord-like material having at least one free end and a portion attached to said anchoring device;
(iii) at least one needle-like member, said at least one needle-like member being attached to said at least one free end of said length of cord-like material; and (iv) an installation tool for deploying said anchoring device within said hole, said installation tool comprising positioning means and retention means wherein:
said positioning means includes a handle, releasably engages said anchoring device and is adapted for locating said anchoring device at a predetermined depth within said hole; and
said retention means is releasably attached to said handle and releasably holds said at least one needle-like member and at least the portion of said length of cord-like material adjacent to said at least one free end;

(b) manipulating said installation tool so as to locate said anchoring device at a preselected depth within said hole with said positioning means;

(c) manipulating said installation tool so as to disassociate said positioning means from said workpiece and to disengage said portion of said length of cord-like material adjacent to said at least one free end from said retention means;

(d) detaching said retention means from said handle;

(e) disengaging said at least one free end of said length of cord-like material and said at least one needle-like member from said retention means; and (f) manipulating said at least one free end of said length of cord-like material and said at least one needle-like member so as to attach said object to said workpiece.

7. A method according to claim 6 wherein
said cord-like material has a curved needle-like member attached to at least one of said free ends; said retention means includes means for releasably holding said needle-like members; and step (d) includes engaging said needle-like member with said retention means.

8. A method according to claim 6 wherein steps (c), (d) and (e) are performed in any order with respect to one another.

9. A method according to claim 6 wherein said retention means comprises a bobbin-like element, said bobbin-like element comprising a central transverse axis, a pair of opposing side portions connected in parallel, aligned and spaced relation to one another by axle means centered on said transverse axis so as to define a continuous groove therebetween;

at least one of said side elements including a peripheral edge, an outwardly facing surface and a radial notch, said radial notch extending into said peripheral edge and communicating with said continuous groove and with said outwardly facing surface; and at least two arcuate projections extending outwardly from said outwardly facing surface of said at least one side portion, said arcuate projections being circumferentially spaced from one another substantially adjacent to said peripheral edge and defining at least one cord-like material/needle-like member retention groove; and each said side portion defining first engagement means centered on said transverse axis and being adapted to rotatably and releasably engage said handle; and wherein said engagement of said free end of said length of cord-like material and said needle-like element with said retention means is accomplished by locating said free end and said needle-like member in said retention groove, drawing a portion of said free end extending from said retention groove inwardly through said notch, drawing said free end into said continuous groove, and wrapping a portion of said free end around said axle.

10. A method according to claim 6 wherein said handle comprises a pair of opposing proximally extending arms adapted to releasably hold said retention means.

11. A method according to claim 10 wherein said handle includes a longitudinal axis, a distal end, a distal portion adjacent said distal end, a proximal end, and a proximal portion adjacent said proximal end, said proximal portion defining said arms and a wall portion, said arms each defining second engagement means adjacent said proximal end of said handle and an inwardly facing planar surface, each said second engagement means being centered on a common axis perpendicular to said longitudinal axis and being adapted to rotatably and releasably engage said engagement means of said retention means, and said wall portion connecting said planar surfaces substantially midway between said proximal end and said distal portion of said handle in a plane transverse to said handle; and wherein said steps of (i) attaching and (ii) detaching said retention means to said handle are accomplished by exerting radially inwardly directed pressure on the portions of said arms located between said connecting wall and said distal portion of said handle so as to spread the portions of said arms located proximally of said wall away from one another by a distance sufficient to allow said retention means to be slid between said arms so as to align said first and second engagement means with one another, and vice versa.

12. A method according to claim 6 wherein said length of cord-like material comprises a length of suture, said anchoring device comprises a suture anchor and said workpiece comprises a piece of bone or bone-like material.

13. A method according to claim 6 wherein said anchoring device comprises (a) a body having a longitudinal axis and a maximum cross-section transverse to said longitudinal axis, (b) at least one elastically deformable barb, each said barb extending from said body, rearwardly and outwardly to an outer end, said outer end being located radially outwardly of an axial projection of said maximum transverse cross-section of said body when said barb is in a nondeformed configuration, and (c) connection means for attaching said portion of said length of cord-like material to said body.

14. A method according to claim 6 wherein said positioning means comprises:

a tubular member and a shaft, said tubular member including a longitudinal axis, a longitudinal lumen extending therethrough, a distal end having a transverse cross-section larger than the transverse cross-section of said hole in said workpiece, and a portion adjacent, and opening into, said distal end adapted to releasably receive a co-axially oriented portion of said anchoring device;

said shaft having a longitudinal axis, a proximal end attached to said handle, a distal end and a distal portion adjacent to said distal end, said distal portion being sized for insertion into said hole in said workpiece;

said shaft also being co-axially, telescopically located in said lumen of said tubular member such that said distal end of said shaft may be reciprocated between:
  (a) a first retracted position wherein said distal end of said shaft resides within said lumen proximally of said portion of said tubular member adapted to receive said anchoring device, and
  (b) a second extended position wherein said distal end of said shaft is located a predetermined axial distance outwardly from said distal end of said tubular member;

wherein said step of engaging said anchoring device with said positioning means comprises co-axially inserting a portion of said anchoring device into said receiving portion of said tubular member when said shaft and said tubular member are in said first retracted position; and wherein said step of manipulating said installation tool so as to position said anchoring device includes locating said distal end of said tubular member in abutting relationship with said workpiece such that said lumen is aligned with said hole, and moving said shaft to said second extended position relative to said tubular member while maintaining said distal end of said tubular member in abutment with said workpiece.

15. A method according to claim 14 wherein said installation tool further comprises means for preventing disengagement of said tubular member from said shaft.

16. A method according to claim 14 wherein said installation tool further comprises means for releasably holding said tubular member in said first retracted position relative to said shaft.

* * * * *